(12) United States Patent
Mathisen

(10) Patent No.: US 10,130,601 B2
(45) Date of Patent: Nov. 20, 2018

(54) USE OF A COMPOSITION COMPRISING FISH OIL AND JUICE FOR THE TREATMENT OF INFLAMMATION

(71) Applicant: Smartfish AS, Oslo (NO)

(72) Inventor: Janne Sande Mathisen, Oslo (NO)

(73) Assignee: Smartfish AS, Oslo (NO)

( * ) Notice: Subject to any disclaimer, the term of this patent is extended or adjusted under 35 U.S.C. 154(b) by 479 days.

(21) Appl. No.: 14/899,101

(22) PCT Filed: Jun. 26, 2014

(86) PCT No.: PCT/NO2014/050116
§ 371 (c)(1),
(2) Date: Dec. 16, 2015

(87) PCT Pub. No.: WO2014/209132
PCT Pub. Date: Dec. 31, 2014

(65) Prior Publication Data
US 2016/0367510 A1    Dec. 22, 2016

(30) Foreign Application Priority Data
Jun. 27, 2013  (NO) .................................. 20130889

(51) Int. Cl.
| | | |
|---|---|---|
| A61K 36/00 | (2006.01) |
| A61K 31/202 | (2006.01) |
| A23L 2/02 | (2006.01) |
| A61K 35/60 | (2006.01) |
| A23L 29/10 | (2016.01) |
| A23L 33/105 | (2016.01) |
| A23L 33/115 | (2016.01) |
| A61K 9/00 | (2006.01) |
| A61K 9/107 | (2006.01) |
| A61K 36/185 | (2006.01) |
| A61K 47/36 | (2006.01) |

(52) U.S. Cl.
CPC .............. *A61K 31/202* (2013.01); *A23L 2/02* (2013.01); *A23L 29/10* (2016.08); *A23L 33/105* (2016.08); *A23L 33/115* (2016.08); *A61K 9/0095* (2013.01); *A61K 9/107* (2013.01); *A61K 35/60* (2013.01); *A61K 36/185* (2013.01); *A61K 47/36* (2013.01); *A61K 36/00* (2013.01)

(58) Field of Classification Search
CPC ..................................................... A61K 36/00
USPC ...................................................... 424/725
See application file for complete search history.

(56) References Cited

U.S. PATENT DOCUMENTS

| 2006/0172012 A1 | 8/2006 | Finley et al. |
| 2007/0167395 A1* | 7/2007 | Eliaz .................... A61K 31/729 514/54 |
| 2010/0291053 A1 | 11/2010 | Clayton et al. |
| 2011/0033602 A1 | 2/2011 | Martinsen |

FOREIGN PATENT DOCUMENTS

| EP | 2279667 A1 | 2/2011 |
| WO | 98/47376 A1 | 10/1998 |
| WO | 2004/075647 A1 | 9/2004 |
| WO | 2007/064222 A1 | 6/2007 |
| WO | 2007/116027 A1 | 10/2007 |
| WO | 2007/149590 A2 | 12/2007 |
| WO | 2009/102845 A2 | 8/2009 |
| WO | 2009/120091 A1 | 10/2009 |
| WO | 2011/005113 A1 | 1/2011 |

OTHER PUBLICATIONS

European Search Report regading corresponding International Application No. PCT/NO2014/050116, dated Nov. 16, 2016, (7 pages).
Written Opinion of the Internal Searching Authority, regarding corresponding International Application No. PCT/NO2014/050116, dated Oct. 16, 2014 (9 pages).
Norwegian Search Report regarding corresponding Norwegian Application No. 20130889, dated Nov. 25, 2013 (3 pages).
Matchynski, J. J. et al., "Combinatorial Treatment of Tart Cherry Extract and Essential Fatty Acids Reduces Cognitive Impairments and Inflammation in the mu-p75 Saporin-Induced Mouse Model of Alzheimer's Disease", Journal of Medicinal Food 16:4 (2013) pp. 288-295.
Yurko-Mauro, K., "Cognitive and Cardiovascular Benefits of Docosahexaenoic Acid in Aging and Cognitive Decline", Current Alzheimer Research 7 (2010) pp. 190-196.
Wu, A. et al., "Dietary Omega-3 Fatty Acids Normalized BDNF Levels, Reduce Oxidative Damage, and Counteract Learning Disability after Traumatic Brain Injury in Rats", Journal of Neurotrauma 21:10 (2004) pp. 1457-1467.
Pallares, V. et al., "Enhanced anti-inflammatory effect of resveratrol and EPA in treated endotoxin-activated RAW 264.7 macrophages", British Journal of Nutrition 108:9 (2012) pp. 1562-1573.
"Fish oil supplements may help to treat COPD", Respiratory Medicine: COPD Update 1:3 (2006) pp. 109-110.
Al-Okbi, S.Y. et al., "Preparation and evaluation of functional foods in adjuvant arthritis", Grasas y Aceites (Sevilla, Spain) 63:4 (2012) pp. 394-402.

(Continued)

*Primary Examiner* — Michael V Meller
(74) *Attorney, Agent, or Firm* — Fitzpatrick, Cella, Harper & Scinto

(57) ABSTRACT

The present invention provides use of a composition comprising fish oil with low totox value and juice in an oil-in-water emulsion in treatment/resolution of inflammation and/or diseases wherein an underlying cause is inflammation. The invention encompasses further said composition comprising acetylsalicylic acid and/or derivatives and/or analogous thereof. Further the present invention is related to the combined use of a composition of the invention and a therapeutic agent for the treatment of inflammatory diseases or diseases wherein an underlying cause is inflammation.

11 Claims, 10 Drawing Sheets

(56) References Cited

OTHER PUBLICATIONS

Cedarbaum, J.M. et al., "The ALSFRS-R: a revised ALS functional rating scale that incorporates assessments of respiratory function", Journal of the Neurological Sciences 169 (1999) pp. 13-21.

Petrescu, F. et al.,"Tumor necrosis factor-α levels in healthy smokers and nonsmokers", International Journal of Chronic Obstructive Pulmonary Disease 5 (2010) pp. 217-222.

Sarir, H. et al., "IL-8 production by macrophages is synergistically enhanced when cigarette smoke is combined with TNF-α", Biochemical Pharmacology 79 (2010) pp. 698-705.

Kuo, P.T. et al., "The fatty acid composition of the serum chylomicrons and adipose tissue of children with cystic fibrosis of the pancreas", The Journal of Pediatrics 60:3 (1962) pp. 394-403.

Underwood, B.A. et al., "Polyunsaturated Fatty Acids and Tocopherol Levels in Patients with Cystic Fibrosis", Annals of the N.Y. Academy of Sciences 203 (1972) pp. 237-247.

Elliott, R.B. et al., "Unusual clinical course in a child with cystic fibrosis treated with fat emulsion", Archives of Disease in Childhood 50:1 (1975) pp. 76-78.

Kusoffsky E. et al., "Prospective Study of Fatty Acid Supplementation Over 3 Years in Patients with Cystic Fibrosis", Journal of Pediatric Gastroenterology and Nutrition 2:3 (1983) pp. 434-438.

Steinkamp G. et al., "Energy Supplements Rich in Linoleic Acid Improved Body Weight and Essential Fatty Acid Status of Cystic Fibrosis Patients", Journal of Pediatric Gastroenterology and Nutrition 31:4 (2000) pp. 418-423.

Maqbool, A. et al., "Serum Linoleic Acid Status as a Clinical Indicator of Essential Fatty Acid Status in Children with Cystic Fibrosis", Journal of Pediatric Gastroenterology and Nutrition 47:5 (2008) pp. 635-644.

Lloyd-Still J. D. et al., "Essential fatty acid deficiency and predisposition to lung disease in cystic fibrosis", Acta Paediatr 85 (1996) pp. 1426-1432.

Lai H. J. et al., "Recovery of Birth Weight z Score within 2 Years of Diagnosis Is Positively Associated with Pulmonary Status at 6 Years of Age in Children with cystic Fibrosis", Pediatrics 123:2 (2009) pp. 714-722.

Oliveira G. et al., "Fatty Acid Supplementation Improves Respiratory, Inflammatory and Nutritional Parameters in Adults with Cystic Fibrosis", Arch Bronconeumol 46:2 (2010) pp. 70-77.

Oliver C. et al., "Omega-3 fatty acids for cystic fibrosis", Cochrane Database of Systematic Reviews 8 (2011) pp. 1-23.

Alicandro G. et al., "A randomized placebo-controlled study on high-dose oral algal docasahexaenoic acid supplementation in children with cystic fibrosis", Prostaglandins, Leukotrienes and Essential Fatty Acids 88 (2013) pp. 163-169.

Strandvik, B., "Relation between Essential Fatty Acid Metabolism and Gastrointestinal Symptoms in Cystic Fibrosis", Acta Paediatica Scandinavica 363 (1989) pp. 58-65.

Jennings, A. et al., "Diet Quality is Independently Associated with Weight Status in Children aged 9-10 Years", Journal of Nutrition 141 (2011) pp. 453-459.

Hu, F. B.et al., "Inflammatory Markers and Risk of Developing Type 2 Diabetes in Women", Diabetes 53 (2004) pp. 693-700.

Weisberg, S. P. et al., "Obesity is associated with macrophage accumulation in adipose tissue", Journal of Clinical Investigation 112:12 (2003) pp. 1796-1808.

Nishimura,S. et al., "CD8+ effector T cells contribute to macrophage recruitment and adipose tissue inflammation in obesity", Nature Medicine 15:8 (2009) pp. 914-920.

McGillicuddy, F.C. et al., "Interferon γ Attenuates Insulin Signaling, Lipid Storage, and Differentiation in Human Adipocytes via Activation of the JAK/STAT Pathway", Journal of Biological Chemistry 284:46 (2009) pp. 31936-31944.

Bakker, G. C. et al., "An antiinflammatory dietary mix modulates inflammation and oxidative and metabolic stress in overweight men: a nutrigenomics approach", American Journal Clinical Nutrition 91 (2010) pp. 1044-1059.

Puglisi, M.J. et al., "Modulation of C-reactive Protein, Tumor Necrosis Factor-α, and Adiponectin by Diet, Exercise, and Weight Loss", Journal of Nutrition 138 (2008) pp. 2293-2296.

Undas, A. et al., "Fibrin Clot Structure and Function, A Role in the Pathophysiology of Arterial and Venous Thromboembolic Disease", Arterioscler Thromb Vasc Biol. 31 (2011) pp. e88-e99.

Undas, A. et al., "Association between atopic diseases and venous thromboembolism: a case-control study in patients aged 45 years or less", Journal Thromb Haemost 9 (2011) pp. 870-873.

Undas, A. et al., "Altered fibrin clot structure/function in patients with idiopathic venous thromboembolism and in their relatives", Blood 114:19 (2009) pp. 4272-4278.

Celinska-Lowenhoff M. et al., "Arterial and venous thrombosis and prothrombotic fibrin clot phenotype in a Polish family with type 1 antithrombin deficiency (antithrombin Krakow)", Thrombosis and Haemostasis 106 (2011) pp. 379-381.

Gajos G. et al., "Reduced Thrombin Formation and Altered Fibrin Clot Properties Induced by Polyunsaturated Omega-3 Fatty Acids on Top of Dual Antiplatelet Therapy in Patients Undergoing Percutaneous Coronary Intervention (OMEGA-PCI Clot)", Arterioscler Thromb Vasc Biol. 31 (2011) pp. 1696-1702.

Moller, J.T. et al., "Long-term postoperative cognitive dysfunction in the elderly: ISPOCD1 study", Lancet 351 (1998) pp. 857-861.

Graham, N.M.H., "The epidemiology of acute respiratory infections in children and adults: a global perspective", Epidemiologic Reviews 12 (1990) pp. 149-178.

Heath, G.W. et al., "Exercise and upper respiratory tract infections. Is there a relationship?", Sports Medicine 14:6 (1992) pp. 353-365.

Haskell, W.L. et al., "Physical activity and public health: updated recommendation for adults from the American College of Sports Medicine and the American Heart Association", Medicine & Science in Sports & Exercise 39:8 (2007) pp. 1423-1434.

Strandvik, B., "Care of Patients with Cystic Fibrosis—Treatment, Screening and Clinical Outcome", Annales Nestle 64 (2006) pp. 131-140.

Peters, E. M. et al., "Ultramarathon running and upper respiratory tract infections. An epidemiological survey", South African Medical Journal 64 (1983) pp. 582-584.

Nieman, D.C., et al., "Infectious episodes in runners before and after the Los Angeles Marathon", The Journal of Sports Medicine and Physical Fitness 30 (1990) pp. 316-328.

Mazzeo, R.S., "The influence of exercise and aging on immune function", Medicine and Science in Sports and Exercise 26:5 (1994) pp. 586-592.

Woods, J.A. et al., "Can exercise training improve immune function in the aged?" Annals of the N.Y. Academy of Sciences 959 (2002) pp. 117-127.

Brinkley, T.E. et al., "Chronic Inflammation Is Associated With Low Physical Function in Older Adults Across Multiple Comorbidities", The Journal of Gerontology Series A: Biological Sciences and Medical Sciences 64A:4 (2009) pp. 455-461.

Bruunsgaard, H. et al., "Special feature: Effects of exercise on the immune system in the elderly population", Immunology and Cell Biology 78 (2000) pp. 523-531.

Gray, P. et al., "Fish oil supplementation augments post-exercise immune function in young males", Brain, Behavior, and Immunity 26 (2012) pp. 1265-1272.

Nieman, D.C. et al., "Relationship between salivary IgA secretion and upper respiratory tract infection following a 160-km race", Journal of Sports Medicine and Physical Fitness 46 (2006) pp. 158-162.

Gleeson, M., et al., "Daily probiotic's (Lactobacillus casei Shirota) reduction of infection incidence in athletes", International Journal of Sport Nutrition and Exercise Metabolism 21 (2011) pp. 55-64.

\* cited by examiner

USE OF A COMPOSITION COMPRISING FISH OIL AND JUICE FOR THE TREATMENT OF INFLAMMATION

CROSS REFERENCE TO RELATED APPLICATIONS

This application is a U.S. National Phase patent application of PCT/NO2014/050116, filed on Jun. 26, 2014, which claims priority to Norwegian Patent Application No. 20130889, filed on Jun. 27, 2013, the disclosures of which are hereby incorporated by reference in the present disclosure in their entirety.

FIELD OF THE INVENTION

The present invention provides use of a composition comprising fish oil with low totox value and juice in an oil-in-water emulsion in treatment/resolution of inflammation and/or diseases wherein an underlying cause is inflammation. The invention encompasses further said composition comprising acetylsalicylic acid and/or derivatives and/or analogous thereof. Further the present invention is related to the combined use of a composition of the invention and a therapeutic agent for the treatment of inflammatory diseases or diseases wherein an underlying cause is inflammation.

BACKGROUND OF THE INVENTION

Omega-3 (n-3) fatty acids have a variety of anti-inflammatory and immune-modulating effects that may be of relevance to diseases and conditions where inflammation is an underlying cause. Inflammation is the body's attempt at self-protection where the aim is to remove harmful stimuli and start the healing process. Inflammation may be divided into acute and chronic inflammation where the acute inflammation starts rapidly and quickly became severe. Examples on acute inflammation may e.g. be acute bronchitis or acute appendicitis. Chronic inflammation may e.g. be failure to eliminate the causing agent, an autoimmune response to a self antigen or a chronic irritant of low intensity that persist. Chronic inflammation may however, mature into severe diseases as chronic obstructive pulmonary disease (COPD), cancer, atherosclerosis, Alzheimer's disease (AD), amyotrophic lateral sclerosis (ALS) etc.

The omega-3 fatty acids are essential to life at any stage, even before birth. They are essential building blocks of the membrane of every cell in the body and their presence are a necessity for maintaining an adequate cell membrane. They do also contribute in the regulation of most biological functions.

The richest dietary source of long-chain omega-3 polyunsaturated fatty acids (PUFA) comes from fish oil. Fatty acids are the building blocks of dietary fats, and are stored substantially in the form of triglycerides. The body cannot however, produce these fatty acids and must obtain them from food sources or from supplements. Three fatty acids compose the omega-3 family: alpha-linolenic acid (ALA), eicosapentaenoic acid (EPA) and docosahexaenoic acid (DHA). ALA is found in e.g. walnuts, some types of beans and olive oils. EPA and DHA are found in fish, including fish oil and supplements.

Resolvins and protectins are oxygenated metabolites derived from EPA and DHA, and a part of the molecular mechanisms contributing to removal of inflammatory cells and restoration of tissue once the need for inflammatory response is over. It has been shown that aspirin treatment enhances the conversion of EPA and DHA to resolvins which carry potent anti-inflammatory signals. The mechanisms by which their effects are exerted are still a matter of controversy, but it seems likely that said oxygenated metabolites plays a significant role as they have potent anti-inflammatory and immunoregulatory actions even in concentrations in the nanomolar and picomolar range. As tissues return to normal, resolvins and protectins together with further oxygenated metabolites as lipoxins and maresins promote resolution of the inflammation through removal of leucocytes and cellular debris.

A recent study at Brigham and Women's Hospital in Boston revealed that omega-3s actually convert into compounds that are 10,000 times more potent than the original fatty acids themselves. These compounds include resolvins, which help bring an inflammatory response in the body to an end.

WO 2007/064222 discloses a composition comprising low oxidized fish oil and juice in an oil-in-water emulsion. There is however, no disclosure of treating and/or resolving inflammation.

From research leading to the present invention it was surprisingly found that the composition comprising low oxidized fish oil and juice in an oil-in-water emulsion may be used in treatment of inflammation and/or diseases wherein an underlying cause is inflammation. The studies which are elaborated below indicate that the inflammatory processes are slowed down and the restoration following inflammation responses are improved following treatment with a composition of the invention comprising fish oil and juice.

SUMMARY OF THE INVENTION

The present invention encompasses a composition comprising a combination of fish oil and juice in an oil-in-water emulsion, for use in treatment of inflammation and/or diseases wherein an underlying cause is inflammation, wherein said fish oil is selected from fish oil having a totox value below 20 and omega-3 content above 10% by weight based on the total weight of the fish oil and wherein a suitable emulsifier is used to stabilize the emulsion.

The present invention relates further to a composition comprising a combination of fish oil and juice in an oil-in-water emulsion and acetylsalicylic acid and/or derivatives thereof in a range of 20 mg to 200 mg per dosage, for use in treatment of inflammation and/or diseases wherein an underlying cause is inflammation, wherein said fish oil is selected from fish oil having a totox value below 20 and omega-3 content above 10% by weight based on the total weight of the fish oil and wherein a suitable emulsifier is used to stabilize the emulsion.

The present invention relates further to the combined use of a composition of the invention and a therapeutic agent for the treatment of inflammatory diseases or diseases wherein an underlying cause is inflammation.

Preferred embodiments are set forth in the dependent claims and in the detailed description of the present invention.

DETAILED DESCRIPTION OF THE INVENTION

Figure 1A:
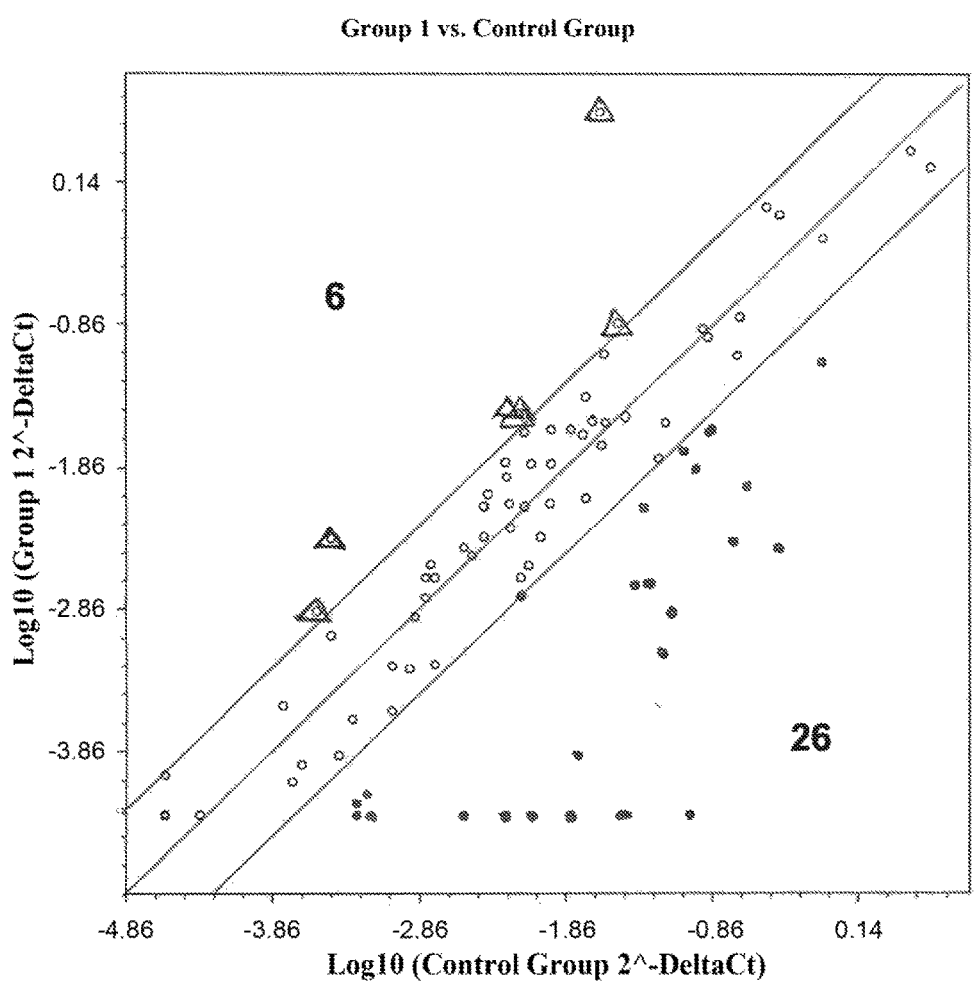
FIG. 1A illustrates the effect of the use of composition of the present invention (Smartfish®) on the ALS baseline transcription of inflammatory mediators. The figures in the left and right corner indicate the number of up regulated and down regulated inflammatory genes respectively. These include the inflammatory cytokines IL1, IL6 etc. and chemokines CXCL3, CCL2 etc. All mRNA levels observed to be up regulated more than 4-fold are indicated as circles with triangle, those that are more than 4-fold down regulated are indicated as filled circles.

It is an object of the present invention to provide use of a composition comprising fish oil and juice in treatment of inflammation and/or diseases/conditions wherein an underlying cause is inflammation. The composition and preparation of the composition are described in WO 2007/064222 which is the inventor's own patent.

The composition used in the present invention has been shown in the following studies to be an omega-3 source with high bioavailability where lipid mediators derived from omega-3 are surprisingly effective delivered and utilized in anti-inflammatory processes in the body.

In the present invention use of the composition in treatment of inflammation and different diseases/conditions wherein an underlying cause is inflammation are studied. Said inflammation or disease/condition are ALS (Amyotrophic lateral sclerosis), AD (Alzheimer's disease) including MCI (mild cognitive impairment), COPD (chronic obstructive pulmonary disease), URTI (upper respiratory tract infections) and overweight and obesity.

Further examples of diseases/conditions to be treated with the composition of the invention are asthma, cystic fibrosis, rheumatoid arthritis, post operative cognitive decline, stroke, coronary disease, diabetes and metabolic frailty.

Also in inflammatory bowel disease, traumatic brain injury (concussions), recovery from stroke, cachexia and sarcopenia should be mentioned as possible conditions were the composition may be beneficial.

A common feature of these diseases is an underlying inflammation, in particular a chronic inflammations.

In the following, various studies and some results are presented:

1. ALS (Amyotrophic Lateral Sclerosis)

The aim of this study was to investigate in vivo baseline inflammatory gene transcription in peripheral blood mononuclear cells and the effects of tozilizumab (Actemra®) in 11 ALS patients and also measure the disability before and after the therapy comparing the FRS-R score (Functional Rating Scale). Fiala et al., (to be published). The patients were free to take nutritional supplements. Three patients were taking the composition used in the present invention, transcription results are presented in Example 1 together with the results from the ALSFRS-R score (The Amyotrophic Lateral Sclerosis Functional Rating Scale).

ALS is an incurable disease and new therapeutic approaches are urgently needed. In ALS patients, inflammation in the spinal cord and peripheral blood is clearly shown. The inflammation is driven by aggregated superoxide dismutase 1 (SOD 1) activation of macrophages through caspase 1, interleukin 1 (IL1), IL6 and chemokine signaling.

In vivo baseline inflammatory gene transcription in peripheral blood mononuclear cells of 11 ALS patients and the effects of tocilizumab (Actemra®) (cytokine antagonist) infusions were studied tocilizumab inhibits global interleukin-6 (IL6) signaling, a key mechanism in chronic rheumatoid disorder.

Patients in the study self-reported the ALSFRS-R score. The Amyotrophic Lateral Sclerosis Functional Rating Scale (ALSFRS-R) is a score from 0-48 which assesses disability in patients with MND. It was developed by Cedarbaum and colleagues (Cedarbaum J M. The ALSFRS-R: a revised ALS functional rating scale that incorporates assessments of respiratory function. BDNF ALS Study Group (Phase III). J Neurol Sci 1999; 169: 13-21). There are twelve questions, some asking about daily activities and how much help a patient needs with them, and some about specific symptoms.

In conclusion it seems that use of the composition of the present invention lowers the expression of inflammatory mRNAs and shows slowing of ALS progression (as measured by decline of the FRS-R score).

Figure 1B:
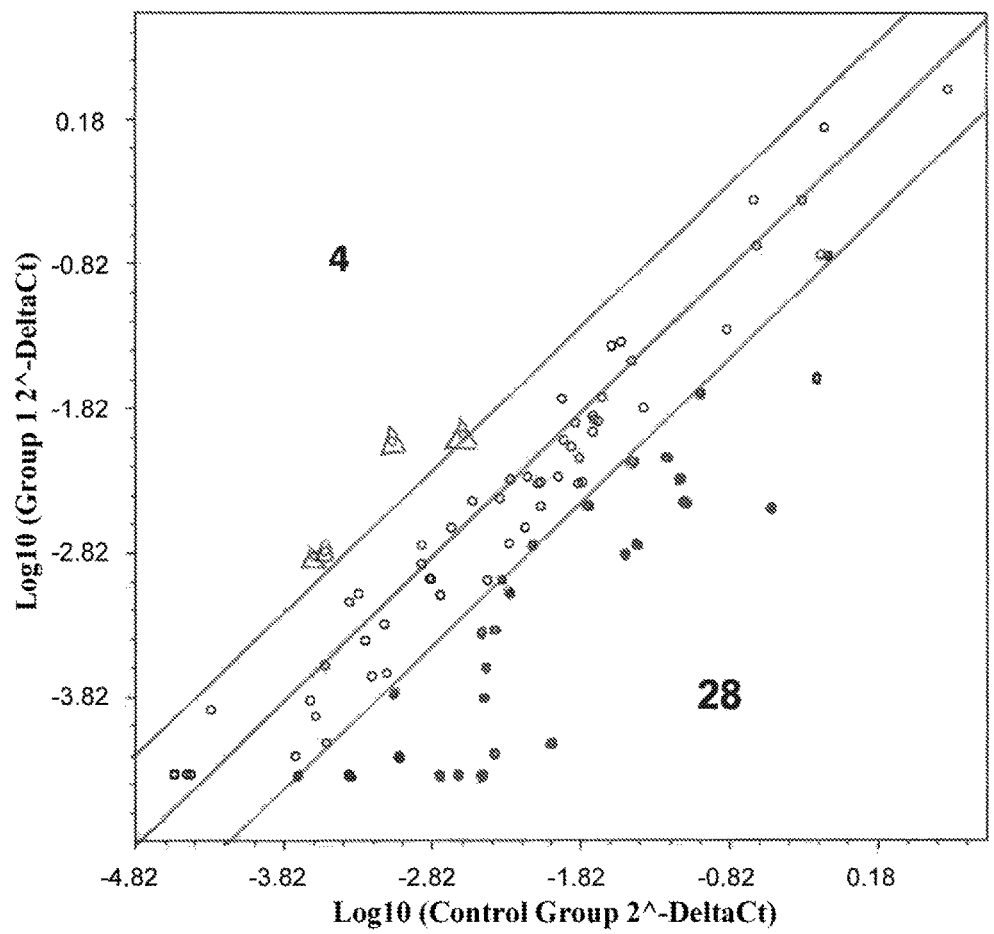
FIG. 1 B illustrates the effect of the use of the composition of the present invention (Smartfish®) on the ALS baseline transcription of inflammatory mediators. The figures in the left and right corner indicate the number of up regulated and down regulated inflammatory genes respectively. These include the inflammatory cytokines IL1, IL6 etc. and chemokines CXCL3, CCL2 etc. All mRNA levels observed to be up regulated more than 4-fold are indicated as circles with triangle, those that are more than 4-fold down regulated are indicated as filled circles.

For further details see Example 1 and FIGS. 1 A and 1 B.

2. Study on Macrophages from ALS Patients

This study is a follow up study of study 1 in the present invention. The aim is to study the production of anti-inflammatory mediators in cell samples from ALS patients and controls.

Macrophage samples from ALS patients and controls are studied. The study includes the study of mediators as e.g.: RvD1, RvD2, RvE1, RvE2, 7Mar1, PGE2, LXA4, 18-HEPE, 17-HDOH.

3. Study in Patients with COPD

The aim of the study is to identify the potential benefit of the composition of the present invention in patients with COPD suffering from severe (hospitalized) exacerbations and to determine the effect and the present invention on biomarkers of airway and systemic inflammation and finally determine the effect of the composition of the present invention on improvements in exercise capacity in patients undergoing a pulmonary rehabilitation.

COPD is a highly prevalent disease caused by an abnormal inflammatory response to inhaled gases and particulates. It is a progressive condition which is manifest by the development of lung pathology affecting the airways and alveolar spaces which results in symptoms which can limit quality of life and functional performance.

The inhaled irritant is usually tobacco smoke, but occupational dust and environmental pollution are variably implicated. The inflammation is characterized by a specific pattern of inflammation, wherein the key inflammatory cells are macrophages, $CD8^+$, T-lymphocytes and neutrophils.

Recent studies have identified that COPD also affects organs other than the lungs and carries a number of systemic manifestations. Current treatment strategies have been targeted at the lung with the use of inhaled therapies the current standard of care. Detailed clinical studies of COPD patients have identified that many individuals manifest evidence of malnutrition, that diet is often poor and that muscle function is compromised. This has led to the development of strategies to augment the nutritional status with oral supplements which are now indicated for patients with a low BMI or history of weight loss.

The development of enriched oral supplements which offer potential additional therapeutic benefits to simply increasing calorie or protein intake is an area that is especially important in the treatment of these patients as they often have increased energy requirements, probably caused by increased respiratory muscle activity and at the same time both chewing and swallowing may be impaired. It is however, previously suggested that diet and nutrition may be an important factor (Schools et al.) in COPD prevention and management since weight loss is an important negative factor.

The patients participating in the study are from 45-80 years of age with confirmed diagnosis. The trial period is up to six months.

For further details see Example 2.

4. COPD 2

This study is a follow up study of study no. 3 above, and comprises a cell study mimicking the condition in COPD wherein inflammatory markers of macrophages and other cells are studied. The aim of the study is to compare the effect of the composition of the present invention on inflammation in the cells, where said cells were subjected to the composition of the present invention, or another composition containing omega-3.

Modifications of inflammatory markers, especially TNF-α and IL-8, are suggested to be of high relevance to COPD. See (*Int J Chronic Obstructive Pulmonary Disease* 2010:5 217-222; *Tumor necrosis factor-alpha levels in healthy smokers and nonsmokers*) and Saris H. et al., *Biochem Pharmacol* 2010, Mar. 1; 79(5(:698-701; *IL-8 production by macrophages is synergistically enhanced when cigarette smoke is combined with TNF-alpha.*

5. Effects of Use of the Composition on Perioperativ Neurocognitive Outcomes.

The aim of this project is to study the effects of omega-3 essential fatty acid supplementation (as a way to increase endogenous resolvins production) on postoperative outcomes after major surgery, including cognitive function and pain, which commonly affect orthopedic surgical patients.

The working hypothesis is that supplementation of the composition of the present invention given for 4 weeks daily, preemptively before surgery, 1) prevents or ameliorates postoperative cognitive decline; 2) alleviates signs of chronic and acute postoperative pain; 3) improves tissue/bone healing after major orthopedic surgery. Using state of the art neuropsychological tests.

As an exploratory aim we are testing the effects of omega-3 supplementation on healthy volunteers to understand how much 4 weeks of daily SmartFish 1100® (the composition of the present invention) affect the omega-3 index (AA:EPA, omega-6:omega-3 in blood) and resolvins production. Overall, this study explores the relationship between resolvins production boosted by omega-3 essential fatty acids and perioperative outcome (cognition, pain, healing).

Surgery and critical illness often lead to cognitive impairments that currently remain without effective preventive treatment. It is estimated that acute cognitive dysfunction (delirium) occurs in 14-24% of patients following general hospitalization, with levels as high as 70% in sub-acute and palliative settings or following admission to the Intensive Care Unit (ICU), frequently seen especially among elderly patients (1). Cognitive trajectories after surgery and delirium can further deteriorate during the first postoperative year leading to prolonged disturbances in multiple domains including learning and memory, concentration, reasoning, abstract thinking, language comprehension, social integration, orientation, and possibly contributing to permanent dementia. Impaired cognitive recovery, whether acute or long lasting, also associates with higher one-year mortality rates, functional decline and represents a significant burden on health care costs.

Using a mouse model of orthopedic surgery, which frequently leads to cognitive dysfunctions in humans, we previously defined a key role of systemic inflammation behind the development of neuroinflammation and surgery-induced cognitive decline. Recently, we reported for the first time a novel role of resolvins in regulating postoperative neuroinflammation and cognitive decline after orthopedic surgery in mice.

Resolvins and protectins are families of local lipid mediators generated from the n-3 fatty acids eicosapentaenoic acid (EPA) and docosahexaenoic acid (DHA) during self-limited resolution of inflammation. Serhan et al. first described these potent anti-inflammatory and specialized proresolving lipid mediators (SPMs) derived from polyunsaturated fatty acids. These include lipoxins derived from arachidonic acid, E-series resolvins derived from the long-chain n-3 fatty acid eicosapentaenoic acid (EPA) and D-series resolvins protectins/neuroprotectins and maresins, all derived from the n-3 fatty acid docosahexaenoic acid (DHA). There is mounting evidence for the role of resolvins in protecting against multiple preclinical disease models, for example renal injury after ischemia reperfusion, experimental colitis, microbial sepsis, stroke amongst others. (RvD1 has also both been implicated as antinociceptive agents reducing inflammatory and postoperative pain in rodent models. Recently, both RvD1 and the 17R epimer AT-RvD1 were identified in peripheral blood of healthy donors, yet no studies have assessed the role of SPMs in the perioperative setting and as biomarkers for poorer surgical prognosis.

For further details see example 3.

6. Study on Cystic Fibrosis

The aim of the study is to investigate the impact of long-term supplementation of fatty acids i.e. the composition of the present invention on clinical status in patients with cystic fibrosis.

It is well known since more than 50 years that patients with cystic fibrosis (CF) have low levels of the essential fatty acid linoleic acid (LA) and also that the long-chain polyunsaturated fatty acid (LCPUFA) DHA is decreased in plasma and tissues (Kuo P T, Huang N N, Bassett D R., J Pediatr 1962; 60:394-403; Underwood B A, Denning C R, Navab M., Ann NY AcadSci 1972; 203:237-47). After 1975, when a newborn recovered in pancreatic function after Intralipid administration (Elliott R B, Robinson P G., Arch Dis Child. 1975 January; 50(1):76-8) several short term trials have been performed showing small effects on growth (Kusoffsky E et al., JPGN 1983; 2(3):434-8; Steinkamp G, et al., JPGN 2000; 34:418-23; Maqbool A et al., JPGN 2008; 47: 635-44) and pulmonary function (Lloyd-Still J D, et al., ActaPediatr 1996; 85:1426-32; Lai H J, et al., Pediatrics. 2009 February; 123(2):714-22). A recent study combining omega-6 and omega-3 fatty acids showed marked improvement in several parameters, compared to supplementation with only omega-3 fatty acids where no clinical benefit were obtained (Oliveira G, et al., tic Arch Bronconeum. 2010; 46(2):70-77 Oliver C, Jahnke N, Cochrane Database SystRev. 2011 Aug. 10; (8):CD002201; Alicandro G, et al., Prostagland Leurkotr Ess Fatty Acids 2013; 88: 163-9). In a long-term small controlled study performed before the gene was identified, improvement was seen in renal and liver parameters (Strandvik B. Acta Paediatr Scand 363: 58-65, 1989; Strandvik B. Ann Nestlé 2006; 64: 131-40). Very long-term, but uncontrolled treatment with omega-6 rich oils and Intralipids have resulted in exceptionally good clinical conditions regarding growth, bone mineral density, pulmonary function, reduction of pulmonary exacerbations and low clinical infectious status in a relatively large patient cohort, the Swedish patients with CF, compared with other international centres (Strandvik B., Ann Nestlé 2006; 64: 131-40). However, it is a lack of long-term controlled studies, so other treatment modalities, as high physical activity from early age, have probably a large importance for the good clinical status in the Swedish patients. In the study 50 patients with CF carrying 2 severe mutations (e.g. dF508, 394delTT) and with pancreatic insufficiency were included. The patients kept to their ordinary treatment of PERT and vitamins and that for the pulmonary symptoms and infections. The patients is randomized to receive fruit juice with LA (900 mg) and the composition of the present invention (DHA 400 mg, EPA 200 mg) or with high oleic sunflower oil (1.5 g) daily for 12 months. Randomization is made by a generator and the 25 ml of juice only numbered so neither patient nor caregivers will be informed by the type of supplementation.

For further details see Example 4.

7. The Composition According to the Present Invention Selectively Improves Insulin Sensitivity in Overweight and Obese Adolescents Wherein Baseline Metabotype Predicts Response The aim of this study was to investigate whether the composition of the present invention, will improve insulin sensitivity in 14-18 year old children.

Dietary intake has changed whereby more children are consuming high-fat, energy-dense and micronutrient-dilute diets (TUNA, 2008). Greater than 56% of Irish adolescents derive >35% energy from dietary fat, and one in three adolescents do not consume fruit at all (IUNA, 2008). This pattern of dietary intake falls outside of healthy eating guidelines and this imbalanced nutrient intake is driving an increase in prevalence of overweight and obesity in this young population (Jennings A, Welch A, van Sluiis E M, Griffin S J, Cassidy A (2011) Diet Quality is independently associated with weight status in children aged 9-10 years. J Nutr. 141(3):453-9).

The emerging model of obesity and diabetes is characterised by sub-acute chronic inflammation and insulin resistance (Hu F B, Meigs J B, Li T Y, Rifai N, Manson J E. Inflammatory markers and risk of developing type 2 diabetes in women. Diabetes 2004; 53:693-700. Irish Universities Nutrition Alliance (TUNA). 2008. National Teen's Food Survey). Mechanistic data indicates inflamed adipose tissue with increased infiltration of immune cells that generate pro-inflammatory cytokines (Weisberg, S. P., et al., Obesity is associated with macrophage accumulation in adipose tissue. J Clin Invest, 2003. 112(12): p. 1796-808; Nishimura, S., et al., CD8+ effector T cells contribute to macrophage recruitment and adipose tissue inflammation in obesity. Nat Med, 2009. 15(8): p. 914-20).

These cytokines, in turn impede insulin sensitivity via down-regulation of critical components of the insulin signalling pathway (McGillicuddy F C, Chiquoine E H, Hinkle C C, Kim R J, Shan R, Roche H M, Smyth E M and Reilly M P (2009) IFNγ attenuates insulin signalling, lipid storage and differentiation in human adipocytes via activation of the JAK/STAT pathway. J Biol Chem. 284(46):31936-44).

Whilst childhood obesity is increasing worldwide, the impact of this pro-inflammatory state and its prediction of the metabolic syndrome and diabetes is relatively unknown in early life.

With childhood obesity increasing at a rapid pace, it is important to establish the role of a non-pharmalogical therapy in decreasing the sub-acute chronic inflammation seen in overweight and obese children. Previous studies have illustrated that in adults, dietary interventions can attenuate the chronic inflammatory state that accompanies obesity (Bakker G C, van Erk M J, Pellis L, Wopereis S, Rubingh C M, Cnubben N H, Koositra T, van Ommen B, Hendriks H F. An anti-inflammatory dietary mix modulates inflammation and oxidative and metabolic stress in overweight men: a nutrigenomics approach. Am J Clin Nutr 2010 April; 91(4): 1044-59).

Several foods contain nutrients that are known to have anti-inflammatory properties (Puglisi M J, Fernandez M L. Modulation of C-reactive protein, tumor necrosis factor-alpha, and adiponectin by diet, exercise, and weight loss. J Nutr. 2008 December; 138(12):2293-6). Such foods include fish as well as fruits and vegetables.

The results from the present study demonstrate heterogeneity with respect to the insulin sensitising effects of the composition of the present invention. Despite similar BMI to non-responders, the insulin resistant and dyslipidaemic metabotype of responders enhanced the impact of anti-inflammatory nutritional approaches. This illustrates potential efficacy optimisation within the context of personalised nutrition.

For further details see Example 5.

8. Study on Diabetes and Coronary Disease

The aim of this study is to investigate whether omega-3 polyunsaturated fatty acids (PUFAs) are involved in the improvement of the biomarkers of coagulation, platelet activation, inflammation and oxidative stress in patients with type 2 diabetes and coronary disease.

Patients with type 2 diabetes and coronary disease are at increased risk of cardiovascular events. Coronary disease is the most frequent cause of morbidity and mortality in diabetic patients. Several mechanisms implicated in the detrimental impact of hyperglycemia in coronary disease have been postulated, i.e., enhanced oxidative stress, the activation of blood coagulation and platelets, stimulation of inflammation, and endothelial cell dysfunction. All of these have also been reported in type 2 diabetes (Undas A, Ariens R A., Arterioscler Thromb Vasc Biol. 2011 Aug. 11. [Epub ahead of print] PubMed PMID: 21836064; Undas A, et al., J Thromb Haemost. 2011 April; 9(4):870-3. doi:10.1111/j.1538-7836.2011.04198.x. PubMed PMID: 21251200; Undas A et al., Blood. 2009 Nov. 5; 114(19):4272-8. Epub 2009 Aug. 18. PubMed PMID: 19690336). Moreover, we have demonstrated that hyperglycemia, both in diabetic patients and under in vitro conditions, is linked with increased thrombin generation and platelet activation, unfavorably altered fibrin clot properties and reduced fibrinolysis.

We have also recently demonstrated that the addition of n-3 PUFA to the combination of aspirin and clopidogrel significantly potentiates platelet response to clopidogrel after percutaneous coronary intervention (Celinska-Lowenhoff M, et al., kow). Thromb Haemost. 2011 August; 106 (2):379-81. Epub 2011 Jun. 9. PubMed PMID: 21655678).

Moreover we have proven that n-3 PUFA added to the standard therapy in coronary artery disease patients undergoing PCI significantly decreases thrombin formation, oxidative stress and favorably alters fibrin clot properties (Gajos G, et al., (OMEGA-PCI clot). Arterioscler Thromb Vasc Biol. 2011 July; 31(7):1696-702. Epub 2011 May 26. PubMed PMID: 21617138).

Those properties on n-3 PUFA might be especially beneficial in patients with coronary diseases and concomitant diabetes.

For further details see Example 6.

9. Study on Exercise Induced Asthma; Respiratory Physiology and Inflammation

The aim of the study is to examine exhaled nitric oxide following provocation tests. The participants take 200 ml Nutrifriend® (the composition of the present invention) twice a day (4 g DHA/EPA per day) before and after exercise. The control group is receiving a drink twice a day at the same time as the study group.

10. Study on the Effect on URTI (Upper Respiratory Tract Infections) in an Athletic Population.

The aim of this study is to investigate the effects of dietary intake of a composition of the invention (hereinafter Smartfish juice or just Smartfish), on the incidence of URTIs in an athletic population.

The effect of exercise on URTI incidence is important to consider not only for competitive athletes and recreational exercisers, but also for particular populations (e.g. the elderly) already at risk due to a compromised immune system.

The results indicated a tendency towards reduced number of URTI episodes per patient and a significant reduction in the total number of symptom days in the group treated with Smartfish.

Thus, the results indicate that a composition of the invention can be used for the treatment of upper respiratory tract infections.

For further details see Example 7.

11. Immunomodulating Effect on LPS Stimulated Macrophages

The aim of this study is to investigate if a composition of the invention (hereinafter Smartfish juice or just Smartfish) has positive effect on inflammatory processes in LPS treated macrophage cell cultures and to compare the effects of the Smartfish juice with that of a good quality fish oil.

From this study it was demonstrated that Smartfish juice reduced the secretion of the proinflammatory cytokine TNF-α from LPS stimulated human macrophages. Further it was demonstrated that Smartfish juice reduced the expression of genes involved in inflammation and stress response (tnf-α, IL8, nfκb, gpx and bax) in LPS stimulated human macrophages. The effect of Smartfish juice was significantly better than the control fish oil of similar good quality.

For further details see Example 8.

12. Resolvin Levels in Macrophages from AD Patients

The aim of the study was to examine the production of the anti-inflammatory mediator resolvin D1 and study whether the composition of the present invention (hereinafter identified Smartfish) had the ability to increase the amount of Resolvin D1 in cell samples from patients suffering from Alzheimers's disease.

As mentioned previously resolvins are oxygenated metabolites derived from EPA and DHA, having potent anti-inflammatory and immunoregulatory actions even in concentrations in the nanomolar and picomolar range.

The results from this study clearly showed that the composition of the invention contributed significantly to an increase in the resolvin level in macrophages.

For further details see Example 9.

The main focus of the above mentioned studies is to reveal the surprisingly beneficial impact of the composition used in the present invention in treatment of inflammation and/or diseases where inflammation is an underlying cause.

The results from these studies indicate that the inflammatory processes are modified and the restoration following inflammation responses are improved. It is therefore believed that use of the composition of the present invention is beneficial to patients subjected to a chronic inflammation, as the composition of the present invention serves the purpose of being a nutritional support, and a disease modifying nutrition active in restoring the balance after inflammation through the supply of omega-3 metabolites important in the healing process.

The composition used in the present invention has been shown to have high stability as marine emulsion and enables low oxidation and keeps the vulnerable nutrients intact and potent which in turn results in increased absorption and high bioavailability.

The composition comprises:

a) fatty acids with a low totox value, especially omega-3 fatty acids in concentrations sufficient to achieve medical and/or nutritional effect(s) and b) juice containing naturally present antioxidants;

c) emulsifier(s)

Different aspects of the composition are described in WO 2007/064222, although further modifications of the composition may be employed in the present invention.

Fish oil in a composition often contributes to an unwanted taste and after taste of fish. The composition for use in the present invention has the advantage of being e.g. a tasteful drink which may be an important prerequisite in patients experiencing changes in taste and loss of appetite.

Accordingly one aspect of the present invention relates to use of a composition comprising a combination of fish oil and juice in an oil-in-water emulsion in treatment of inflammation and/or diseases wherein an underlying cause is inflammation, wherein said fish oil is selected from fish oil having a totox value below 20 and omega-3 content above 10% by weight based on the total weight of the fish oil, and wherein a suitable emulsifier is used to stabilize the emulsion.

Use of the composition of the invention may be beneficial in the treatment of any inflammation or disease wherein an underlying cause is inflammation.

In the present invention use of the composition in treatment of inflammation and different diseases/conditions wherein an underlying cause is inflammation are studied. Said inflammation or disease/condition are ALS (Amyotrophic lateral sclerosis), AD (Alzheimer's disease) including MCI (mild cognitive impairment), COPD (chronic obstructive pulmonary disease), URTI (upper respiratory tract infections) and overweight and obesity.

In another embodiment the composition of the present invention may be used in the treatment of diseases selected from the group or any combinations thereof, asthma, cystic fibrosis, rheumatoid arthritis, post operative cognitive decline, stroke, coronary disease, diabetes and metabolic frailty.

Also in inflammatory bowel disease, traumatic brain injury (concussions), recovery from stroke, cachexia and sarcopenia should be mentioned as possible conditions were the composition may be beneficial.

The fish oil may be selected from any fish oil preparation of appropriate quality, i.e. the level of oxidation should be low. To be of appropriate quality the level of oxidation given as the totox-value (2 times the peroxide value (PV) added with the anisidine value (AV)) should be below 20. In a preferred embodiment the totox value may be below 10. Such fish oils of appropriate quality are usually clear oils with a very mild fishy odour and taste.

The content of omega-3 fatty acids differs widely in different fish oil preparations. It is preferable that the content of omega-3 fatty acids is high. According to preferred embodiments, the content of omega-3 fatty acids in the fish oil used in the composition of the invention should be at least 10%, preferably at least 16%, or most preferably above 30% by weight based on the weight of the fish oil.

One preferred embodiment of the present invention provides a composition wherein the content of the fish oil is about 0.5%-15% by weight based on the total weight of the composition, more preferably in the range of 2%-7%, most preferably about 2%-5%.

In further embodiments of the present invention the content of the juice is about 20-95% by weight based on the total weight of the composition. The juice may be selected from fruit and/or berries having a suitable high level of antioxidants. It is further preferred that the fruit possess a minimum level of metal ions functioning as oxidizing agent.

Preferred juices may be selected from the following group:
pomegranate, apricot, grapefruit, orange, cranberry, rosehip, pineapple, black chokeberry, mulberry, cloudberry, acerola, raspberry, watermelon, peach, grapes, cherry, jambolao, apple, mango, pear, aronia, passionfruit, lemon and kiwi. Further, the juice may be selected from beetroot, carrot, lingonberry (cowberry), guava, blackberry or greens like kale, spinach, celery, parsley or cucumber. Any juice suitable for stabilizing the oxidation of the fish oil may, however, be used. The juice may be prepared by adding water to juice concentrates and juice purée obtaining a normal ready-to use juice. The juice may also be a fresh pressed juice.

Further the composition used according to the invention may comprise yoghurt powder or other powders such as hemp milk powder, almond milk powder or oat milk powder. By adding such additives, the composition thickens giving an inviting consistency. The amount added may be in the range of 5-10% by weight based on the total weight of the composition.

In one embodiment the composition is free of any milk ingredients.

The composition may further be added vitamins preferably Vitamin D. As an example the amount of vitamin D is from 1 µg to 2000 µg per unit dose of 200 ml, preferably from 5 µg to 50 µg per unit dose of 200 ml, most preferably 10 µg to 20 µg per unit dose of 200 ml. Vitamin B including folic acid may also be added. Also minerals like selenium and zinc may be added.

To stabilize the oil-in-water emulsion comprising fish oil and juice suitable emulsifiers are be used. Suitable emulsifier may be selected from the following group: milk solids, whey protein, oat protein and pea protein. The emulsifier may be e.g. Grindsted or Lacprodan, but any suitable emulsifier may be employed. Further the present invention may comprise thickening agent which preferably may be pectin preferably from oat, more preferably from fruit e.g. citrus.

In a further preferred embodiment of the present invention the composition may comprise sweeteners, flavouring agents, antioxidants and preservatives. Preferred preservative and sweetener may be potassium sorbate and xylitol respectively.

A preferred antioxidant according to the present invention is tocopherol.

In one embodiment, the composition are not added any additional antioxidant not naturally present.

In a further preferred embodiment of the present invention the composition for administration may be at a dosage in a range from about 300 mg/day to about 5000 mg/day of EPA and DHA, preferably about 3000 mg/day, more preferably about 2000 mg/day and most preferably about 1100 mg/day. In order to achieve therapeutically effect, the dosage may be lower or even higher. The composition may be administered as a drink in a volume range of 50-300 ml, preferably 100 ml, more preferably 200 ml. The person in need of the composition of the invention may drink one or several unit doses of the drink per day. Body weight etc. will be parameters to be used in the dosage calculation, the dosage may therefore vary from one individual to another.

In a preferred embodiment of the present invention the composition may be drinkable, in a capsule or in a powder form.

In a further embodiment the composition of the invention may be used as an adjuvant therapy or in combination with other therapeutic agents used to treat the specific disease or disorder such as conventional drugs used to treat the inflammatory disease in question or the diseases wherein an underlying cause is inflammation.

The term "in combination" means that the composition of the invention and the other therapeutic agent are administered in such an amount and separated by such administration times as to produce a therapeutic effect. The composition of the invention and the other therapeutic agent may be administered simultaneously or sequential for the use in the treatment of inflammation of diseases wherein an underlying cause is inflammation. The composition of the invention and the other therapeutic agent may be in the form of separate formulations or formulated together in a combined formulation. Included in "other therapeutic agent" is radiotherapy.

Different aspects of the composition are described in WO 2007/064222, although further modifications of the composition may be employed in the present invention. Thus an aspect of the present invention relates to said composition comprising acetylsalicylic acid and/or derivatives and/or analogous thereof and the use of said composition for use in treatment of inflammation and/or diseases wherein an underlying cause is inflammation.

It has recently been shown that aspirin helps trigger the production of resolvins, it was further reported that the aspirin triggered the production of a longer acting form of resolvin D3 trough a different pathway. These resolvins shut off, or resolve the inflammation underlies the destructive conditions such as inflammatory lung disease, heart disease and arthritis.

In one embodiment said inflammation and/or diseases wherein an underlying cause is inflammation are ALS (Amyotrophic lateral sclerosis), AD (Alzheimer's disease) including MCI (mild cognitive impairment), COPD (chronic obstructive pulmonary disease), URTI (upper respiratory tract infections) and overweight and obesity.

In another embodiment the composition of the present invention may be used in the treatment of diseases selected from the group or any combinations thereof, asthma, cystic fibrosis, rheumatoid arthritis, post operative cognitive decline, stroke, coronary disease, diabetes and metabolic frailty.

Also in inflammatory bowel disease, traumatic brain injury (concussions), recovery from stroke, cachexia and sarcopenia should be mentioned as possible conditions were the composition may be beneficial.

Accordingly an aspect of the present invention relates to a use of a composition comprising a combination of fish oil and juice in an oil-in-water emulsion and acetylsalicylic acid and/or derivatives thereof in a range of 20 mg to 200 mg per dosage, wherein said fish oil is selected from fish oil having a totox value below 20 and omega-3 content above 10% by weight based on the total weight of the fish oil, and wherein a suitable emulsifier is used to stabilize the emulsion.

The fish oil may be selected from any fish oil preparation of appropriate quality, i.e. the level of oxidation should be low. To be of appropriate quality the level of oxidation given as the totox-value (2 times the peroxide value (PV) added with the anisidine value (AV)) should be below 20. In a preferred embodiment the totox value may be below 10. Such fish oils of appropriate quality are usually clear oils with a very mild fishy odour and taste.

The content of omega-3 fatty acids differs widely in different fish oil preparations. It is preferable that the content of omega-3 fatty acid is high. According to preferred embodiments, the content of omega-3 fatty acids in the fish oil used in the composition of the invention should be at least 10%, preferably at least 16%, or most preferably above 30% by weight based on the weight of the fish oil.

One preferred embodiment of the present invention provides a composition wherein the content of the fish oil is about 0.5%-15% by weight based on the total weight of the composition, more preferably in the range of 2%-7%, most preferably about 2%-5%.

In one embodiment of the present invention the content of acetylsalicylic acid may be in the range of 20 to 2000 mg/dosage, preferably 50 to 1000 mg/dosage, more preferably from 80 to 500 mg/dosage. Even lower or higher doses may be preferable.

In further embodiments of the present invention the content of the juice is about 20-95% by weight based on the total weight of the composition. The use may be selected from fruit and/or berries having a suitable high level of antioxidants. It is further preferred that the fruit possess a minimum level of metal ions functioning as oxidizing agent.

Preferred juices may be selected from the following group:
pomegranate, apricot, grapefruit, orange, cranberry, rosehip, pineapple, black chokeberry, mulberry, cloudberry, acerola, raspberry, watermelon, peach, grapes, cherry, jambolao, apple, mango, pear, aronia, passionfruit, lemon and kiwi. Further, the juice may be selected from beetroot, carrot, lingonberry (cowberry), guava, blackberry or greens like kale, spinach, celery, parsley or cucumber. Any juice suitable for stabilizing the oxidation of the fish oil may, however, be used. The juice may be prepared by adding water to juice concentrates and juice purée obtaining a normal ready-to use juice. The juice may also be a fresh pressed juice.

Further the composition used according to the invention may comprise yoghurt powder or other powders such as hemp milk powder, almond milk powder or oat milk powder. By adding such additives, the composition thickens giving an inviting consistency. The amount added may be in the range of 5-10% by weight based on the total weight of the composition.

In one embodiment the composition is free of any milk ingredients.

The composition may further be added vitamins preferably Vitamin D. As an example the amount of vitamin D is from 1 µg to 2000 µg per unit dose of 200 ml, preferably from 5 µg to 50 µg per unit dose of 200 ml, most preferably 10 µg to 20 µg per unit dose of 200 ml. Vitamin B including folic acid may also be added. Also minerals like selenium and zinc may be added.

To stabilize the oil-in-water emulsion comprising fish oil and juice suitable emulsifiers are be used. Suitable emulsifier may be selected from the following group: milk solids, whey protein, oat protein and pea protein. The emulsifier may be e.g. Grindsted or Lacprodan, but any suitable emulsifier may be employed. Further the present invention may comprise thickening agent which preferably may be pectin preferably from oat, more preferably from fruit e.g. citrus.

In a further preferred embodiment of the present invention the composition may comprise sweeteners, flavouring agents, antioxidants and preservatives. Preferred preservative and sweetener may be potassium sorbate and xylitol respectively.

A preferred antioxidant according to the present invention is tocopherol

In one embodiment, the composition are not added any additional antioxidant not naturally present.

In a further preferred embodiment of the present invention the composition for administration may be at a dosage in a range from about 300 mg/day to about 5000 mg/day of EPA and DHA, preferably about 3000 mg/day, more preferably about 2000 mg/day and most preferably about 1100 mg/day. In order to achieve therapeutically effect, the dosage may be lower or even higher. The composition may be administered as a drink in a volume range of 50-300 ml, preferably 100 ml, more preferably 200 ml. The person in need of the composition of the invention may drink one or several unit doses of the drink per day. Body weight etc. will be parameters to be used in the dosage calculation, the dosage may therefore vary from one individual to another.

In a preferred embodiment of the present invention the composition may be drinkable, in a capsule or in a powder form.

EXAMPLES

Example 1

ALS
Peripheral blood nuclear cells (PBMSs) of the 10 ALS patients showed either up regulation (group 1) or down regulation (group 2) of inflammatory genes in comparison to age matched controls at baseline. At base line one half of the ALS subjects had strong inflammatory activation (Group 1) (8 genes up regulated >4-fold, P<0.05 vs. controls) and the other half (Group 2) had weak activation (Group 2). All patients showed greater than four-fold up regulation of MMP 1, CCL7, CCL13 and CCL24. Tocilizumab infusions in Group 1 patients were associated with down regulation of inflammatory genes, whereas in the patient in group 2 with up regulation of these genes.

The inflammation is present in the peripheral blood as inflammatory genes for cytokines (interleukin-1β (IL1β), IL6, TNFα) and the chemokines (CCL3, CCL20, CXCL2, CXCL3, CXCL5) are highly up regulated in peripheral blood mononuclear cells ALS patients in Group 1.

Two of the patients receiving the composition of the present invention showed a strong down regulation of inflammatory genes.

In one of said patients 6 genes were up regulated and 26 genes were down regulated. In the baseline of group 1, 11 genes were up regulated and 21 down regulated. In the control 10 genes were up regulated and 24 genes were down regulated (FIG. 1 A). In the second of said patients 4 genes were up regulated and 28 genes were down regulated. In the baseline of group one 8 genes were up regulated and 13 genes were down regulated (FIG. 1 B).

In conclusion it seems that the use of the composition of the present invention is lowering the expression of inflammatory mRNAs.

A comparison of the FRS-R scores before Actemra® therapy in all patients in Group 1 (high inflammation) and Group 2 (low inflammation) suggests that the decline per month in group 1 was higher (range 0.59 to 2.6) than I Group 2 (range 0.3 to 0.7) Table 1, Five patients have been treated with (Actemra®) no. 1 for 8 months, no. 2 for 2 months, no. 6 for 4 months, no 7 for 5 months, and no. 11 for 4 months (Table 1). Three patients showed strong attenuation of the loss of FRS-R points per month no. 1: 2.6 loss to 0.4 loss, no. 6: from 0.7 loss to 1 point gain, no. 11: from 3.5 loss to 0.5 loss. Said three patients were the patients receiving the composition of the present invention. In conclusion it seems that the use of the composition is slowing of ALS progression (as measured by decline of the FRS-R score).

Example 2

COPD

The study design is a Randomized Placebo Controlled Clinical Trial.

The study population is subjects admitted to hospital with a primary diagnosis of exacerbation of COPD eligible for early rehabilitation scheme. 20 subjects 10 on each treatment arm. The patients are between 40-80 years of age. The patient receives the composition of the present invention.

The Inclusion Criteria are:
1. Patients 45-80 years of age admitted to UHS with a confirmed diagnosis of COPD and a primary admitting diagnosis of exacerbation of COPD.
2. Willingness to provide written consent for participation in the study.
3. Subjects able to participate in all study procedures.

The Exclusion Criteria are:
1. Patients unable to ingest oral supplements or placebo.
2. Patients with known intolerance to any of components of the supplement or placebo.
3. Patients requiring intubation and ventilation or non-invasive ventilation during the admission.
4. Patients already receiving oral nutritional supplements.
5. Patients taking long term oral corticosteroids or other systemic immunosuppressive medication.
6. Subjects with co-morbidities which in the opinion of the investigator would confound study outcomes including an active cancer diagnosis, uncontrolled diabetes mellitus, uncontrolled cardiac conditions including arrhythmias, cardiac failure and angina, TB, dementia.
7. Any subject deemed in the opinion of the investigator not clinically suitable to participate in the study.

The Assessment Methods are:
1) Clinical Indices of Symptoms, Physiological variables and associated adverse events.
2) Clinical laboratory evaluations (for severity, immune responses and biomarkers) performed on blood, exhaled air and sputum.
3) Changes in Lung function and measures of functional status and body composition.
4) Daily Diary of Respiratory Symptoms Statistical Methods:
Demography: descriptive statistics is provided.
Adverse events: is described.
MITT analysis of differences in outcomes between treatment and placebo arms.

TABLE 1

| # | Age, Sex | ALS Type | ALS Group** | ALS Duration (months) *** | FRS-R change Before Actemra$^R$ or first visit (points/mo) | FRS-R change After Actemra$^R$ (points/mo)***** |
|---|---|---|---|---|---|---|
| 1 | 59, M | Spinal | Group 1 | 24 | −2.6 | −0.4 |
| 2 | 55, F | Spinal | Group 1 | 38 | −1.3 | −0.75 |
| 3 | 52, F | Spinal | Group 1 | 20 | −0.75 | ND |
| 4 | 51, M | Spinal and bulbar | Group 1 | 28 | −1.0 | ND |
| 5 | 50, F | Spinal | Group 1 | 23 | −0.59 | ND |
| 6 | 65, M | Spinal | Group 2 | 11 | −0.7 | +1.0 |
| 7 | 72, M | Spinal | Group 2 | 16 | −0.37 | −2.0 |
| 8 | 55, M | Spinal | Group 2 | 48 | −0.47 | ND |
| 9 | 26, M | Spinal | Group 2 | 35 | −0.37 | ND |
| 10 | 58, M | Spinal and bulbar | Group 2 | 11 | −0.3 | ND |
| 11 | 63, M | Spinal | Group unknown | 8 | −3.5 | −0.5 |

*Patient #
**Group 1 = strong inflammation; Group 2 = weak inflammation
*** at first blood test

Example 3

Perioperative Neurocognitive Outcomes

Study Design:

Randomized placebo-controlled design includes patients undergoing elective total hip replacement under regional or general anesthesia.

Power Analyses.

Elderly at-risk patients >65 years (males and females) scheduled for orthopedic surgery is included in the study after oral and written informed consent. Patientsis randomized to drink SmartFish® (omega-3 supplementation group) or placebo control drinks for 4 weeks before surgery.

Inclusion Criteria:
1. Patients over 65 years old, males and females. ASA physical status I-II
2. Total hip replacement
3. Obtained consent Exclusion Criteria:
1. Patient's refusal to participate in the trial
2. Ongoing smoking/nicotine use
3. Disabling neuropsychiatric disorders (MMSE score ≤24, diagnosis of dementia, Alzheimer, Parkinson, schizophrenia, mental depression) or other signs of significant cognitive decline
4. History of stroke with neurological sequalae
5. Surgical procedure scheduled for regional anesthesia
6. Severe cardiac and/or renal and/or hepatic impairment
7. Coagulopathy
8. Terminal phase of a chronic disease
9. Patients on non-steroidal anti-inflammatory drugs (NSAIDs)
10. Admission on B-Glucose >15 mmol/L of poorly controlled diabetes mellitus
11. Presumed uncooperativeness or legal incapacity
12. Preoperative or later postoperative B-hemoglobin <90 g/L
13. BMI value >25 or <18.5
14. Food allergies, lactose intolerance or other ingredients present in the drink Subject Withdrawal:

Study subjects are free to permanently discontinue their participation in the scheduled study assessments at any time without providing a reason or the study subjects can be permanently discontinued by their legal representative as well. The study subjects can also permanently discontinue their participation in the study if it is recommended for any medical reason by the investigator. All reasons of withdrawal are recorded on the participant CRF.

Overview of the Study Design:

Approximately 4 weeks before surgery, consented subjects is randomized using a computer-generated code to receive SmartFish® (the composition of the present invention) or Placebo Control drinks. Information is collected on:
1. Demographics (body weight, length, BMI) and routine vital sign recording (e.g. blood pressure, pulse rate).
2. Venous blood sampling (a total volume of 10 ml venous blood for inflammatory biomarkers, ex-vivo whole blood test and omega-3 index).
3. Preoperative cognitive test batter (according to ISPOCD protocol, see Moller J T et al, Lancet 1998).
4. Pain ad modum NPS.

Prior to surgery, patients admit to the preoperative unit in order to undergo:
1. Body weight, and routine vital sign recording
2. Venous blood sampling (a total volume of 10 ml venous blood for inflammatory biomarkers, ex-vivo whole blood test and omega-3 index)
3. Preoperative cognitive test batter (according to ISPOCD protocol)
4. Pain NPS (cumulative pain assessment)

On the day of surgery, a member of the research group is again applying the electronic CRF to record standard vital signs before, during, after the surgical procedure. During surgery 5 ml of blood is collected at the time of the implant insertion and 5 ml at the end of surgery to measure inflammatory biomarkers. Urine is collected up to 24 hours after surgery. Patients are then transferred to the postoperative unit where additional vital signs is recorded including pain and PONV scoring ad modum VAS. Postoperative pain is assessed during the first 72 hours after surgery by recording NPS twice daily, i.e. in the morning and evening. Per 24 hours, the total consumption of IV and oral paracetamol (mg/24 h), non-steriodal anti-inflammatory compounds (mg/24 h) and opioids (mg/24 h, after conversion to peroral opioidal equivalents) is recorded in both study groups. After 72 hours, daily measurements of NPS (morning and evening) as well as the consumption of NSIAD (mg/24 h) and opioids (mg/24 h after conversion to peroral opioidal equivalents) is collected by self-administered patients questionnaires.

From the first to the third postoperative day continuous recording of relevant vital signs including sleep diary, pain and PONV scores is performed.

One week after surgery (or as close as possible), patients return to the preoperative unit in order to record:
1. Routine vital sign and analyses of B-hemoglobin in order to insure a postoperative hemoglobin level >90 g/L (see above for exclusion criteria)
2. Venous blood sampling (a total volume of 10 ml venous blood for inflammatory biomarkers and omega-3 index)
3. Postoperative cognitive test battery (according to ISPOCD protocol)

Three months (approximately 90 days) after surgery, patients return to the preoperative unit in order to record:
1. Routine vital sign and analyses of B-hemoglobin in order to insure a postoperative hemoglobin level >90 g/L (see above for exclusion criteria)
2. Venous blood sampling (a total volume of 10 ml venous blood for inflammatory biomarkers, ex-vivo whole blood test, omega-3 index and additional 10 ml for genetic analyses of inflammatory biomarkers)
3. Postoperative cognitive test batter (according to ISPOCD protocol)

All following parts of the study protocol, vital sign data, cognitive test results, laboratory tests and related information on pain, PONV and sleep hygiene are recorded in an electronic CRF and kept in a computer for further analyses.

Example 4

Cystic Fibrosis 50 patients with CF carrying 2 severe mutations (e.g. dF508, 394delTT) and with pancreatic insufficiency are included after informed consent. Exclusion criteria will be pregnancy, transplantation and age below 6-7 years (due to the size of capsule and pulmonary function tests). The patients keep to their ordinary treatment of PERT and vitamins and that for the pulmonary symptoms and infections.

The patients are randomized to receive the composition of the present invention comprising fruit juice (the composition of the present invention) with LA (900 mg) and ω3-LCPUFA (DHA 400 mg, EPA 200 mg) or with olive oil (1.5 g) daily for 12 months. Randomization is made by a generator and the 200 ml of juice only numbered so neither patient nor caregivers are informed by the type of supplementation.

Methods:

A food registration (24 hr recall) is performed at start and end of treatment, including a food frequency questionnaire. An extra 24 hr recall is performed at 6 months for control that no change occurs in the ordinary diet related to fatty acids.

At the start and end of study will a yearly check-up of the CF patients are performed so no extra investigations have to be done except a urinary sample for analysis of 8-isoprostane (to check for lipid peroxidation). Plasma cytokines and routine infection parameters (WBC, CRP, Ig G, IL-6, Il-8) and liver function tests (ASAT, ALAT, γGT, PK) and renal tests (urea, creatinine) are checked at start and end. Pulmonary testing, including NO and FEV1 are also included in the yearly check-up. The number of infection exacerbations are compared with the same time the year before in all patients Outcome:

Primary outcome: Growth (weight, height, BMI, skin fold, MMAC).

Secondary outcome: Number of infections and antibiotic treatments. Infection parameters.

Example 5

Overweight and Obesity

The composition according to the present invention selectively improves insulin sensitivity in overweight and obese adolescents wherein baseline metabotype predicts response.

Introduction

Anti-inflammatory nutritional approaches may attenuate obesity-induced insulin resistance. However, results from clinical studies are not entirely consistent, warranting increased focus on determinants of inter-subject variability particularly within young cohorts at high-risk. Baseline metabotype may partially discriminate responders from non-responders.

The Method of the Study:

Metabolic effects of the composition of the present invention were determined in overweight and obese adolescents (n=58; mean±SD age 15.9±1.6y; BMI 32.1±6.5 kg/m$^2$) by an 8-wk randomized, crossover, placebo-controlled intervention. Subjects who demonstrated >10% improvement in HOMA-IR (Homeostatic model assessment; a model for quantifying insulin resistance) were categorized as responders.

Results:

The composition of the present invention acted as an anti-inflammatory nutritional supplementation and selectively reduced HOMA-IR in 40% of subjects (responders; supplement −32.05±18.02% v placebo 13.13±54.09%, p=0.004). In comparison with non-responders, responding subjects demonstrated an adverse pre-treatment metabotype characterized by increased HOMA-IR, total cholesterol and LDL cholesterol despite similar BMI (p=0.001, p=0.029, p=0.024, p=0.236, respectively). Stepwise multiple regression analysis confirmed baseline HOMA-IR and LDL:HDL ratio as significant independent predictors of HOMA-IR response to anti-inflammatory supplementation ($R^2$=0.432, p<0.001). On-going analysis is defining the molecular basis of the differential response.

Conclusion:

These results demonstrate heterogeneity with respect to the insulin sensitizing effects of the composition of the present invention. Despite similar BMI to non-responders, the insulin resistant and dyslipidaemic metabotype of responders enhanced the impact of anti-inflammatory nutritional approaches. This illustrates potential efficacy optimization within the context of personalized nutrition.

Table 2 below shows the inflammatory markers pre and post supplementation of the composition of the present invention and placebo in overweight and obese adolescents (n=23).

TABLE 2

Inflammatory markers pre and post anti-inflammatory and placebo supplementation in overweight and obese adolescents (n23)

| | Supplement | | Placebo | | |
| --- | --- | --- | --- | --- | --- |
| | Pre | Post | Pre | Post | P value |
| Total Adiponectin (μg/ml) | 7.76 (4.79) | 8.21 (5.52) | 7.46 (3.71) | 7.38 (3.69) | 0.46 |
| HMW Adiponectin (μg/ml) | 3.73 (2.72) | 4.22 (3.36) | 3.81 (2.21) | 3.39 (2.50) | 0.05 |
| CD163 (ng/ml) | 749.83 (251.13) | 705.76 (267.69) | 724.11 (274.81) | 667.14 (244.80) | 0.74 |
| Complement C3 (mg/ml) | 0.66 (0.38) | 0.54 (0.30) | 0.64 (0.36) | 0.61 (0.42) | 0.50 |
| PBMC TNF-a unstimulated (pg/ml) | 78.89 (194.81) | 7.86 (3.31) | 42.93 (153.00) | 8.53 (3.64) | 0.49 |
| PBMC TNF-a LPS stimulated (pg/ml) | 284.24 (242.02) | 304.20 (199.56) | 367.70 (550.15) | 274.88 (252.30) | 0.44 |
| PBMC IL-6 unstimulated (pg/ml) | 166.88 (251.27) | 37.56 (73.17) | 73.44 (147.90) | 66.18 (144.64) | 0.13 |

TABLE 2-continued

Inflammatory markers pre and post anti-inflammatory and placebo supplementation in overweight and obese adolescents (n23)

| | Supplement | | Placebo | | |
| --- | --- | --- | --- | --- | --- |
| | Pre | Post | Pre | Post | P value |
| PBMC IL-6 LPS stimulated (pg/ml | $0.9 \times 10^4$ $(0.9 \times 10^4)$ | $1.1 \times 10^4$ $(0.7 \times 10^4)$ | $0.8 \times 10^4$ $(1.0 \times 10^4)$ | $1.1 \times 10^4$ $(0.9 \times 10^4)$ | 0.81 |

Table 3 below shows the anthropometrical and biochemical characteristics at baseline and after supplementation of the composition of the present invention compared to placebo supplementation for eight weeks in overweight and obese boys (n=23).

Anthropometrical and biochemical characteristics at baseline and after anti-inflammatory nutrient supplementation compared with placebo supplementation for 8 wk in overweight and obese boys (n = 23)

| | Supplement | | Placebo | | |
| --- | --- | --- | --- | --- | --- |
| | Pre | Post | Pre | Post | P value |
| Weight (kg) | 101.60 (22.24) | 101.58 (22.29) | 101.56 (22.98) | 101.91 (22.76) | 0.69 |
| Body Mass Index (kg/m²) | 32.18 (5.94) | 31.94 (6.02) | 32.25 (6.29) | 32.11 (6.19) | 0.76 |
| Body Mass Index Z-Score | 2.73 (0.72) | 2.69 (0.73) | 2.74 (0.73) | 2.72 (0.75) | 0.67 |
| Waist Circumference (cm) | 109.52 (14.03) | 108.97 (14.37) | 109.27 (13.59) | 108.10 (14.75) | 0.83 |
| Fat Mass (kg) | 34.37 (16.99) | 33.34 (15.79) | 34.29 (17.96) | 34.90 (18.22) | 0.05 |
| Lean Body Mass (kg) | 67.55 (11.35) | 68.55 (11.4) | 66.40 (10.58) | 66.68 (10.12) | 0.68 |
| Systolic Blood Pressure (mmHg) | 126 (13) | 131 (15) | 127 (22) | 130 (17) | 0.24 |
| Diastolic Blood Pressure (mmHg) | 66 (10) | 66 (10) | 73 (15) | 74 (20) | 0.44 |
| Glucose (mmol/L) | 5.12 (0.35) | 5.13 (0.41) | 5.22 (0.34) | 5.25 (0.34) | 0.57 |
| Insulin (mU/L) | 12.39 (8.28) | 11.29 (5.28) | 12.61 (9.01) | 11.56 (6.68) | 0.72 |
| HOMA-IR | 2.87 (2.00) | 2.61 (1.34) | 2.97 (2.29) | 2.68 (1.55) | 0.69 |
| QUICKI | 0.34 (0.03) | 0.34 (0.02) | 0.33 (0.02) | 0.34 (0.02) | 0.61 |
| TAG (mmol/L) | 1.09 (0.50) | 0.99 (0.41) | 1.10 (0.45) | 1.10 (0.43) | 0.28 |
| Total Cholesterol (mmol/L) | 3.58 (0.60) | 3.67 (0.57) | 3.68 (0.69) | 3.73 (0.63) | 0.66 |
| HDL Cholesterol (mmol/L) | 1.07 (0.23) | 1.07 (0.20) | 1.12 (0.23) | 1.09 (0.18) | 0.50 |
| LDL Cholesterol (mmol/L) | 2.01 (0.43) | 2.15 (0.40) | 2.06 (0.48) | 2.14 (0.46) | 0.38 |
| LDL-HDL | 1.93 (0.44) | 2.07 (0.48) | 1.87 (0.47) | 2.00 (0.51) | 0.86 |
| APO A1 (mg/dL) | 107 (19) | 103 (14) | 110 (17) | 106 (14) | 0.93 |
| Total Adiponectin (µg/ml) | 5.81 (3.13) | 6.50 (3.98) | 6.24 (4.98) | 6.07 (3.72) | 0.27 |
| HMW Adiponectin (µg/ml) | 2.82 (3.35) | 2.89 (3.00) | 2.77 (3.26) | 2.16 (2.06) | 0.02 |
| CD163 (ng/ml) | 711.42 (288.21) | 704.50 (306.93) | 708.77 (250.61) | 698.60 (294.95) | 0.90 |
| complement C3 (mg/ml) | 0.51 (0.31) | 0.49 (0.31) | 0.59 (0.38) | 0.78 (0.43) | 0.16 |
| PBMC TNF-a unstimulated (pg/ml) | 18.53 (31.30) | 41.41 (148.64) | 9.98 (8.32) | 12.88 (14.72) | 0.29 |
| PBMC TNF-a LPS stimulated (pg/ml) | 299.52 (175.39) | 346.56 (268.11) | 389.41 (348.36) | 25.61 (530.03) | 0.38 |
| PBMC IL-6 unstimulated (pg/ml) | 93.42 (180.74) | 95.83 (218.29) | 47.85 (90.04) | 042.65 (102.08) | 0.44 |
| PBMC IL-6 LPS stimulated (pg/ml) | $1.2 \times 10^4$ $(0.9 \times 10^4)$ | $1.1 \times 10^4$ $(0.8 \times 10^4)$ | $1.2 \times 10^4$ $(0.7 \times 10^4)$ | $1.2 \times 10^4$ $(0.8 \times 10^4)$ | 0.21 |

Table 4 below shows baseline characerstics of responders and non-responders to supplementation of the composition of the present invention.

Baseline Characteristics of Responders and Non-responders to anti-inflammatory supplementation

|  | Responders (38%) | Non-responders (62%) | P-value |
|---|---|---|---|
| Age | 16.05 (1.95) | 16.07 (1.55) | 0.949 |
| Weight (kg) | 95.98 (24.41) | 91.27 (22.08) | 0.431 |
| Body Mass Index (kg/m$^2$) | 33.20 (7.07) | 31.03 (6.17) | 0.159 |
| Waist Circumference (cm) | 107.43 (13.90) | 103.75 (14.36) | 0.238 |
| Body fat % | 39.25 (3.74) | 35.62 (10.31) | 0.150 |
| Glucose (mmol/L) | 5.22 (0.36) | 5.19 (0.37) | 0.760 |
| Insulin (mU/L) | 15.18 (8.49) | 9.50 (4.16) | 0.001 |
| HOMA-IR | 3.57 (2.12) | 2.23 (1.06) | 0.002 |
| QUICKI | 0.32 (0.02) | 0.35 (0.03) | 0.002 |
| TAG (mmol/L) | 1.01 (0.49) | 0.95 (0.45) | 0.539 |
| Total Cholesterol (mmol/L) | 4.05 (0.75) | 3.66 (0.64) | 0.037 |
| HDL Chloesterol (mmol/L) | 1.26 (0.22) | 1.19 (0.32) | 0.356 |
| LDL Cholesterol (mmol/L) | 2.33 (0.58) | 2.04 (0.48) | 0.045 |
| Total adiponectin (μg/ml) | 7.76 (4.79) | 7.45 (3.50) | 0.872 |
| HMW adiponectin (μg/ml) | 3.73 (2.72) | 3.83 (3.20) | 0.926 |
| CD163 (ng/ml) | 749.83 (251.13) | 634.30 (308.11) | 0.047 |
| Complement C3 (mg/ml) | 0.66 (0.38) | 0.51 (0.26) | 0.378 |
| PBMC TNFa | 78.89 (194.81) | 16.53 (27.49) | 0.100 |
| PBMC IL-6 | 166.88 (251.27) | 93.22 (193.12) | 0.272 |

Figure 2:
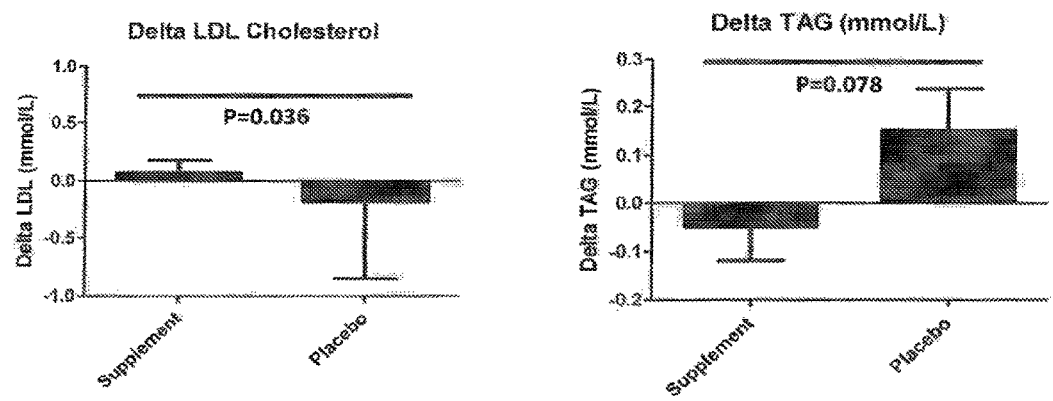
FIG. 2 illustrates metabolic response to the supplementation of the composition of the invention and the placebo in the responders
Figure 3:
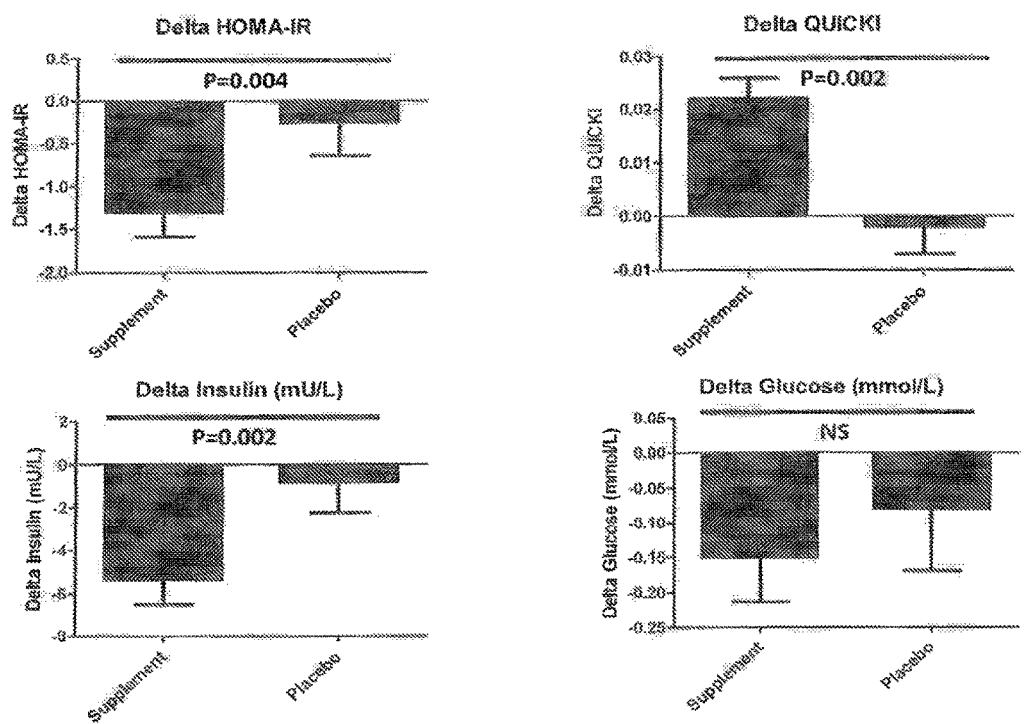
FIG. 3 illustrates the change in values (mmol/L) of delta LDL cholesterol and delta TAG response to the supplementation of the composition of the invention and placebo supplementation.

See also FIGS. 2 and 3

Example 6

Diabetes and Coronary Disease

This study is a prospective, single-center, double-blind, placebo-controlled, randomized study.

Patients with diabetes and coronary disease are randomly assigned to receive the composition of the present invention comprising 1000 mg of eicosapentaenoic and 1000 mg of docosahexaenoic acids in a clinical nutrition composition (n-30) or placebo (n-30) for 3-6 months (depending on the funding). Basic parameters of blood counts (RBC, WBC, HO and platelets), inflammation and kidney markers are assessed.

Some of the specific coagulation tests are measured twice: at the beginning of study and at the end of treatment period. We plan to do: fibrin generation tests, plasma levels of thrombin-antithrombin (TAT) complexes, prothrombin fragment 1.2, plasma fibrin clot permeability (Ks) and 8-iso-prostaglandin F2alpha (8-iso-PCF2alpha, an oxidative stress marker). For detailed list of biomarkers see Table 5 (final list will depend on funding). Vascular and endothelial functions are assessed by brachial artery flow-mediated dilatation (FMD) and hyperemic shear stress (HSS) tests.

TABLE 5

Established cardiovascular markers tested for the potential influence of n-3 PUFA in patients with diabetes and coronary disease

| Cardiovascular markers | Methods |
|---|---|
| Circulating triglycerides | Colorimetric |
| Lipoproteins | |
| TG/HDL | Colorimetric |
| TC/HDL | Colorimetric |

TABLE 5-continued

Established cardiovascular markers tested for the potential influence of n-3 PUFA in patients with diabetes and coronary disease

| Cardiovascular markers | Methods |
|---|---|
| Circulating triglycerides | Colorimetric |
| Inflammation (Galli & Calder, 2009) | |
| CRP | latex nephelometry |
| IL-6 | ELISA |
| TNF-a | ELISA |
| Oxidative stress | |
| Isoprostane (8-iso-PGF2alpha) | ELISA |
| Ox-LDL | ELISA |
| Immuno-modulators | |
| ICAM-1 | ELISA |
| VCAM-1 | ELISA |
| Coagulation system | |
| Fibrinogen | Von Clauss method |
| International Normalized Ratio (INR) | ISI calibration method |
| prothrombin 1.2 fragments | ELISA |
| Endogenous Thrombin Potential (ETP) | Thrombinoscope BV, |
| Fibrin clot properties | As Ref. 6. |
| Endothelium function | |
| Asymmetric Dimethylarginine (ADMA) | HPLC |
| Lipoprotein-associated Phospholipase A2 (Lp-PLA2) | ELISA |
| Apoptotic markers (Fas ligand, Ga6) | ELISA |

Example 7

Study on the Effect on URTI (Upper Respiratory Tract Infections) in an Athletic Population Background Info to Study One of the leading causes of a visit to GPs are upper respiratory tract infections (URTI), such as coughs, colds, ear infections, pharyngitis and laryngitis (Graham, 1990, The epidemiology of acute respiratory tract infections in children and adults: a global perspective. *Epidemiologic Reviews* 12, 149-178). Furthermore it has been demonstrated that, on average, every adult will suffer from between 2 and 5 colds every year (Heath et al., 1992, Exercise and upper respiratory tract infections. Is there a relationship? *Sports Med* 14, 353-365) making the socioeconomic cost, for example in work days lost and medical expenses, of these illnesses quite considerable. It is therefore imperative that we have a good understanding of any mechanisms which are known to reduce the risk of URTI and thus alleviate the associated socioeconomic burden.

It is well established that exercise is beneficial to health, and current recommendations indicate that every adult should accumulate 30 min of exercise on 5 days of the week (Haskell et al., 2007, Physical activity and public health: updated recommendation for adults from the American College of Sports Medicine and the American Heart Association. *Med Sci Sports Exerc* 39, 1423-1434). Recently evidence has been mounting to support the hypothesis that high-intensity exercise is more effective than low/moderate intensity exercise in improving health (Babraj et al., 2009, Infectious episodes in runners before and after the Los Angeles Marathon. *J Sports Med Phys Fitness* 30, 316-328). However, increasing the volume and intensity of exercise undertaken may also have some detrimental consequences, such as increased risk of URTI. Indeed two epidemiological studies showed that, in athletes recovering after an acute bout of endurance exercise, the incidence of URTI was two-fold greater following exercise compared to non-exercised controls (Peters & Bateman, 1983, Ultramarathon running and upper respiratory tract infections. An epidemiological survey. *S. Afr. Med J* 64, 582-584; Nieman et al., 1990, Infectious episodes in runners before and after the Los Angeles Marathon. *J Sports Med Phys Fitness* 30, 316-328). Further investigations have found similar results after a wide variety of exercise and sports.

The effect of exercise on URTI incidence is important to consider not only for competitive athletes and recreational exercisers, but also for particular populations (e.g. the elderly) already at risk due to a compromised immune system (for review see Mazzeo, 1994, The influence of exercise and aging on immune function. *Med Sci Sports Exerc* 26, 586-592). Aging processes include a decrease in immune function thought to be partially responsible for the increased incidence of fatal bacterial and viral infections in the elderly population (Woods et al., 2002, Can exercise training improve immune function in the aged? *Ann N Y. Acad Sci* 959, 117-127). Ageing is also often associated with a chronic low-grade inflammation, indicated by increased levels of inflammatory cytokines and acute phase proteins which correlate closely with functional limitations (Brinkley et al., 2009, Chronic Inflammation Is Associated With Low Physical Function in Older Adults Across Multiple Comorbidities. *The Journals of Gerontology Series A: Biological Sciences and Medical Sciences* 64A, 455-461). In order to overcome or reduce such functional changes, the elderly population is encouraged to participate in physical activity to improve muscle function and disease onset. On the other hand, such exercise could also be detrimental to elderly subjects who clearly show a substantial attenuation in their immune function compared to a young people (Bruunsgaard & Pedersen, 2000, Special feature for the Olympics: effects of exercise on the immune system: effects of exercise on the immune system in the elderly population. *Immunol Cell Biol* 78, 523-531). It is therefore imperative to identify any possible strategies which can be employed to improve immune function after exercise in a wide variety of populations allowing them to gain the benefits of regular exercise while reducing the risk of URTI.

One possible method which may be employed to enhance immune function is to alter the nutritional intake of essential fatty acids. The n-3 polyunsaturated fatty acids (PUFAs), eicosapentaenoic acid (EPA) and docosahexaenoic acid (DHA), both found in fish oils, have been shown to have immunomodulatory effects in vitro. Furthermore in a recent study we have carried out we found that fish oil consumption could enhance natural killer (NK) cell activity and peripheral blood mononuclear cell (PBMC) IL-2 production (Gray et al., 2012. Fish oil supplementation augments post-exercise immune function in young males. *Brain, Behavior, and Immunity* in press.). What is not clear, however, is whether these immune changes have any effect on the incidence of URTIs.

Trial Objective and Purpose

The aim of the current project is to investigate the effects of dietary intake of a composition of the invention (hereinafter Smartfish juice or just Smartfish), on the incidence of URTIs in an athletic population.

Trial Design

Participants 60 healthy volunteers (male and female) between the ages of 18-45 will be recruited to the study. Participants will be recruited by contacting local athletics/sports clubs. They will be participating in at least 3 hours of moderate to high intensity training per week. Participants will be excluded if they have a history of cardiovascular, metabolic or haematological disorders which will be determined via a preliminary health screen questionnaire. Participants will be asked to refrain from taking any dietary supplements for the duration of the study.

Pre-Experimental Procedures

A pre-supplementation saliva sample will be obtained. This involves participants passively drooling into a pre-weighed bijou tube for 3 min. The tub will then be weighed again to allow calculation of salivary flow rate.

Experimental Protocol

Participants will be randomly assigned (matched for gender) to either a control group or a Smartfish group for the 16 weeks of the study. The Smartfish group will consume the composition of the invention as two fruit juice based drinks per day containing 0.5 g of EPA and 0.5 g of DHA, per drink, for a total of 2 g per day of combined EPA/DHA. The placebo group will receive the same drinks, minus the EPA and DHA. Both placebo and fish oil drinks will be provided by the company Smartfish AS.

Randomization will be carried out by an independent third party who will generate a random number table. The participants will be asked to supplement their diet in this way for a 16 week period.

During this period we will ask participants to record their physical activity levels on a weekly basis using the international physical activity questionnaire (IPAQ: https://sites.google.com/site/theipaq/). On a daily basis participants will also be asked to complete the Wisconsin Upper Respiratory Symptom Survey (WURSS) and record any over the counter or prescription remedies taken for any colds/coughs etc. Participants will be given stamped addressed envelopes with which to post these forms back on a weekly basis and also the option to fill these in electronically.

Sample Analysis

Salivary IgA and lysozyme will be measured to give an indication of salivary antimicrobial status and due to the correlation between these markers and the incidence of URTI (e.g. Nieman et al., 2006. Relationship between salivary IgA secretion and upper respiratory tract infection following a 160-km race. *J Sports Med Phys Fitness* 46, 158-162.). This analysis will be carried out using commercially available ELISA kits.

Statistics

As this is a preliminary pilot study a formal power calculation is not being undertaken. We have designed the study to include the number of subjects used in similar studies (Gleeson et al., 2011, Daily probiotic's (*Lactobacillus casei* Shirota) reduction of infection incidence in athletes. *Int J Sport Nutr Exerc Metab* 21, 55-64.) looking at dietary interventions to reduce the incidence of URTIs.

Data will be analyzed by a two way repeated measures ANOVA and paired t-tests where appropriate.

Results

Figure 4:
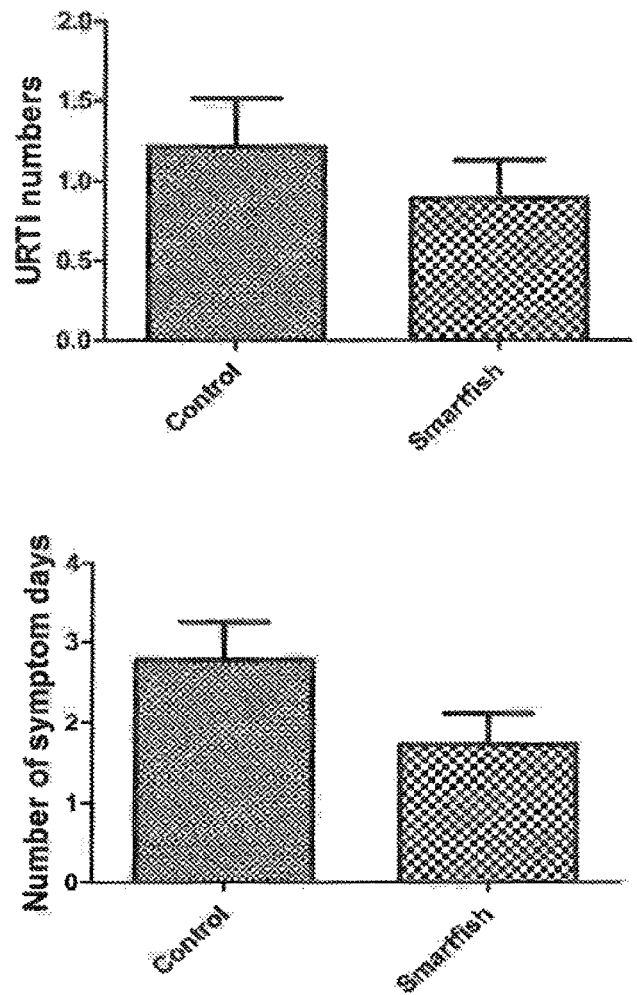
FIG. 4 illustrates the effect of a composition of the invention (Smartfish) on patients suffering from URTI (upper respiratory tract infections) during the 16 week intervention period compared. URTI patients not supplemented with Smartfish served as a control group. Upper panel illustrates the average number of URTI episodes per patient in each group. The lower panel illustrates the total number of symptoms per day in each group.

FIG. 4 illustrates results from patients suffering from URTI (upper respiratory tract infections) in control and Smartfish groups of the 16 week intervention period. Although not significant there is a tendency towards reduced number of URTI episodes per patient in the group treated with Smartfish, as outlined in FIG. 4 upper panel. Further, there is a significant (P<0.05) reduction in the total number of symptom days in the Smartfish group compared to the control group.

Thus, the results clearly indicate that a composition of the invention can be used for the treatment of upper respiratory tract infections.

The study is ongoing and further data will be available at a later stage.

Example 8

Immunomodulating Effect on LPS Stimulated Macrophages
Background

The aim of the study is to test if a composition of the invention (hereinafter identified Smartfish juice or just Smartfish) has positive effects on inflammatory processes and to compare the effects of the Smartfish juice with that of good quality fish oil.

Macrophages are important for regulation of immune response and development of inflammation. In tissue and culture macrophages differentiate from monocytes. Many different chemical substances are produced by these cells (including cytokines, enzymes, complement proteins, and regulatory factors) and the cells also stimulate other immune cells. LPS is an important component of the outer membrane of gram negative bacteria and induces expression of inflammatory cytokines (such as tumor necrosis factor alpha (TNF alpha) and interleukin 6 (IL-6) in macrophages and endothelial cells. LPS stimulation of human monocytes has been shown to activate many intracellular signaling pathways including IkappaB kinase (IKK)-NF-kappaB signaling pathways and three mitogen activated protein kinase signaling pathways (ERK1 and 2, JNK and p38) (Guha et al., 2001). These signaling pathways activate transcription factors such as NF-kappaB (p50/p65) and AP-1 (c-Fos/c-Jun), which coordinates the induction of many genes for inflammatory mediators. Several inflammatory cytokines are induced by oxidative stress and will induce release of other cytokines and increase oxidative stress. This makes cytokines important in chronic inflammation and other immune responses.

Addition of LPS to the macrophages in culture initiates the inflammatory response and is therefore a good model system to test the effects of Smartfish juice on inflammatory reactions.

Materials and Methods
Cell Culture

Cells were maintained at 37° C. with 5% $CO_2$ in a humidified incubator and all cell culture solutions were obtained from Invitrogen (Invitrogen, Carlsbad, Calif., USA).

THP-1 cells, normally growing in suspension, were obtained from the American Type Culture Collection (Manassas, Va., USA). THP-1 cells were cultured in RPMI 1640 medium containing 10% FCS, 0.05 mM 2-mercaptoetanol, 2 mmol/1 L-glutamine, 100 U/mL penicillin and 100 μg/mL streptomycin. Cells were sub-cultured 3 times a week. Differentiation into a macrophage-like phenotype was achieved by treating THP-1 cells in 12 well culture plates (1 mL cell suspension with $10^6$ cells/mL per well) with 100 ng/mL phorbol 12-myristate 13-acetate (PMA, Sigma-Aldrich) for 72 h. Adherent, differentiated cells were washed twice with pre-warmed culture medium (RPMI as above, but without mercaptoethanol) and rested for 48 h before onset of the experiment.

Differentiated THP-1 cell mono-cultures were stimulated with Smartfish, a good quality 1812 fish oil or serum-DMSO control at the concentrations indicated for 24 hours before addition of 0.5 ng/ml LPS (E. coli 055:B5). Supernatants were collected after 6 h of incubation.

Smartfish juice (Nutrifriend 2000 [2500 mg omega-3, 2000 mg EPA/DHA]) and the good quality 1812 fish oil (TOTOX below 20) were added to the cells at the same concentration with regard to EPA and DHA. The concentration of EPA and DHA in the fish oil was 19.6 times higher than in Smartfish. Thus, 0.5 mg/ml fish oil and 9.8 mg/ml Smartfish were added to the cells as an emulsion with serum and DMSO.

The experiment was run in duplicate and repeated 4 times.
ELISA

IL-6 and TNF-alpha concentrations in cell culture supernatants were determined using an enzyme-linked immunosorbent assay (ELISA). Monoclonal mouse anti-human IL-6 or TNF-alpha antibody (BD Bioscience Pharmingen, San Diego, Calif., US) suspended in coating buffer (0.1 M Carbonate/Bicarbonate buffer pH 9.6) was added to Maxi-iSorp™ ELISA plates (Nunc, Roskilde, Denmark) and incubated over night at 4° C. Plates were washed three times with PBS containing 0.01% Tween-20 and unspecific binding-sites were blocked by incubating with 5% BSA in PBS for 1 h at room temperature. After washing five times with PBS-Tween, samples and human recombinant IL-6 or TNF-alpha standards (BD Bioscience Pharmingen,) diluted in working strength high performance ELISA (HPE) buffer from Sanquin (Amsterdam, Netherlands) were added to the plates, which were then incubated for 1.5 h at room temperature followed by washing five times with PBS-Tween. Plates were then incubated for 1 h with biotinylated mouse anti-human IL-6 or TNF-alpha monoclonal antibody (BD Bioscience Pharmingen) in HPE buffer. After another washing step streptavidin-horseradish peroxidase conjugate (BD Bioscience Pharmingen) in HPE buffer was added and incubated at room temperature for 30 min. Plates were then washed five times with 30 sec between each wash. Colour developed after addition of 3,3',5,5'-tetramethylbenzidine (Sigma-Aldrich) in 0.05 M Phosphate-Citrate-Buffer containing H2O2. After 10 min the reaction was stopped by addition of 1 N H2SO4, and absorbance was measured at 450 nm using the Spectrostar Nano plate reader (BMG LABTECH, Offenburg, Germany).

Gene Expression

RNA was isolated using RNeasy Plus mini kit (Qiagen, Valencia, Calif., USA). Concentration and purity of RNA were evaluated using NanoDrop 1000 Spectrophotometer (NanoDrop Technologies, USA). cDNA was made from 300 ng RNA in a 20 μL reaction volume by using Taqman reverse transcriptase reagents (Applied Biosystems, Foster City, Calif., USA). The cDNA synthesis was run in a PCR machine under the following conditions: 25° C. for 10 minutes, 48° C. for 60 minutes, and 95° C. for 5 minutes. The reaction mix for qPCR consisted of 4 μl diluted (1:10) cDNA, 1 μl forward and reverse primer (final concentration of 0.5 μM; Table 6), and 5 μl SYBR Green-I Master (Roche Applied Science, Germany). A standard curve was included for each primer pair to evaluate the primer efficiency. All samples were analyzed in parallels, and a non-template control with water substituted for cDNA was run for each primer pair. The qPCR reaction was run on a LightCycler480 (Roche Diagnostics Gmbh, Germany) under the following conditions: Preincubation at 95° C. for 5 minutes, amplification with 45 cycles at 95° C. for 15 seconds and 60° C. for 1 minutes, melting curve at 95° C. for 5 seconds and 65° C. for 1 minutes, cooling at 40° C. for 10 seconds. The relative gene expression level was calculated according to the ΔΔCt method (Pfaffl 2001) using ef1a as reference gene.

TABLE 6

| Gene | Access. no. | Forward (5'-3') | Reverse (5'-3') |
|---|---|---|---|
| nfkb | nm_03998 | GAGGAAGAAAATGGTGGAGTCTGGG | TCCTCCGAAGCTGGACAAACACA |
| gpx2 | nm_002083 | GGGGCTCACTCTGCGCTTCA | GCCCTGCCCCGGAACGTATT |
| ef1a | NM_001402.5 | GACACGTAGATTCGGGCAAGTCCA | CCATCTCAGCAGCCTCCTTCTCAA |
| rpol2 | NM_000937.4 | GCGCAATGAGCAGAACGGCG | ACTTCTGCATGGCACGGGGC |
| Bax | NM_138761 | TCCAGGATCGAGCAGGGCGA | GTCTGTGTCCACGGCGGCAA |
| tnfa | NM_000594 | GTTGTAGCAAACCCTCAAGCTG | GAGGTACAGGCCCTCTGATG |
| IL8 | NM_000584 | TGTGAAGGTGCAGTTTTGCCA | CCCAGTTTTCCTTGGGGTCC |

Results and Discussion
Cytokine Secretion

Figure 5:
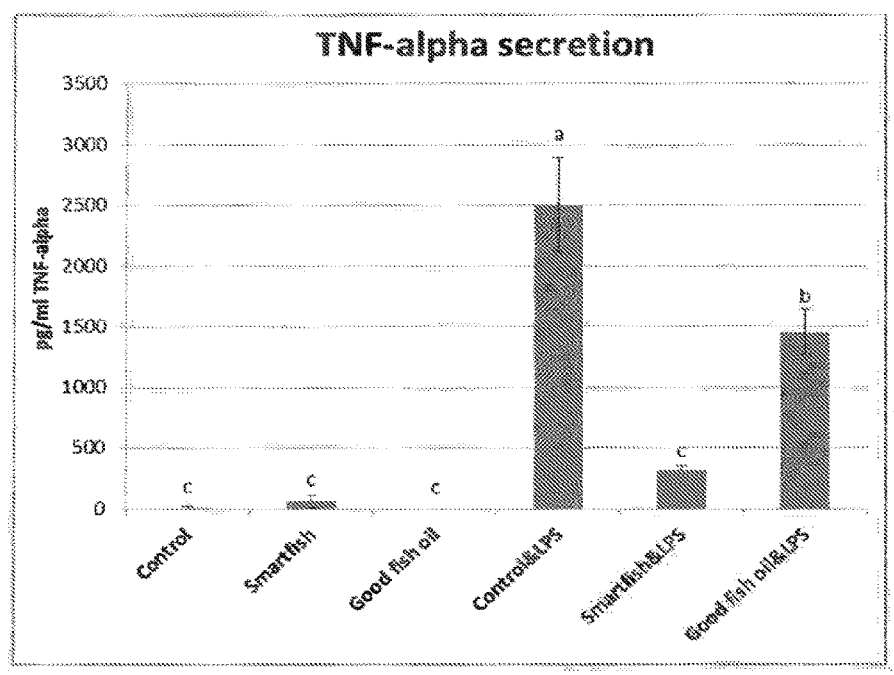
FIG. 5 illustrates the effect of a composition of the invention (Smartfish) and good fish oil on the secretion of the proinflammatory cytokines TNF-α from LPS stimulated macrophages analysed by ELISA.

The effect of Smartfish and the good fish oil on the secretion of the proinflammatory cytokines TNF-α and IL-6 was analysed by ELISA. Smartfish and the good fish oil had no significant effect on the basal secretion of TNF-α (FIG. 5). Addition of LPS to simulate an inflammation response significantly increased the secretion of TNF-α in control cells from 11 pg/ml to 2500 pg/ml. Addition of good fish oil significantly decreased the LPS-induced secretion of TNF-α compared to control. Interestingly, addition of Smartfish had an even stronger reducing effect on LPS-induced TNF-α secretion than the good fish oil, reducing the TNF-α secretion to a level comparable to basal secretion.

Figure 6:
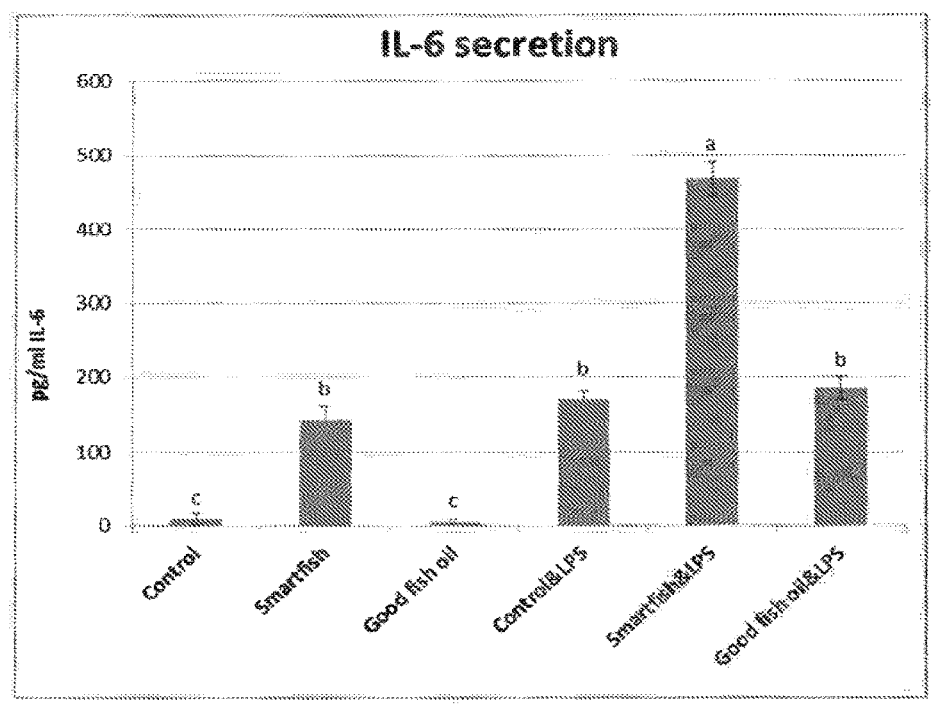
FIG. 6 illustrates the effect of a composition of the invention (Smartfish) and good fish oil on the secretion of the proinflammatory cytokines IL-6 from LPS stimulated macrophages by ELISA.

The secretion profile obtained for IL-6 differed from the profile obtained for TNF-α (FIG. 6). Smartfish significantly increased both the basal and the LPS-induced secretion of IL-6 compared to control and good fish oil, while the good fish oil had no significant effect on LPS-induced secretion of IL-6 compared to control. The same good fish oil has previously reduced the LPS-induced secretion of IL-6 in THP-1 derived macrophages. The reason for this discrepancy is not obvious. However, IL-6 can act as both a pro-inflammatory and anti-inflammatory cytokine. As an anti-inflammatory cytokine IL-6 has an inhibitory effect on TNF-α. Thus, in this experiment IL-6 may act as an anti-inflammatory cytokine, and this is in line with the inhibitory effects seen on LPS-induced secretion of TNF-α.

Gene Expression

Figure 7:
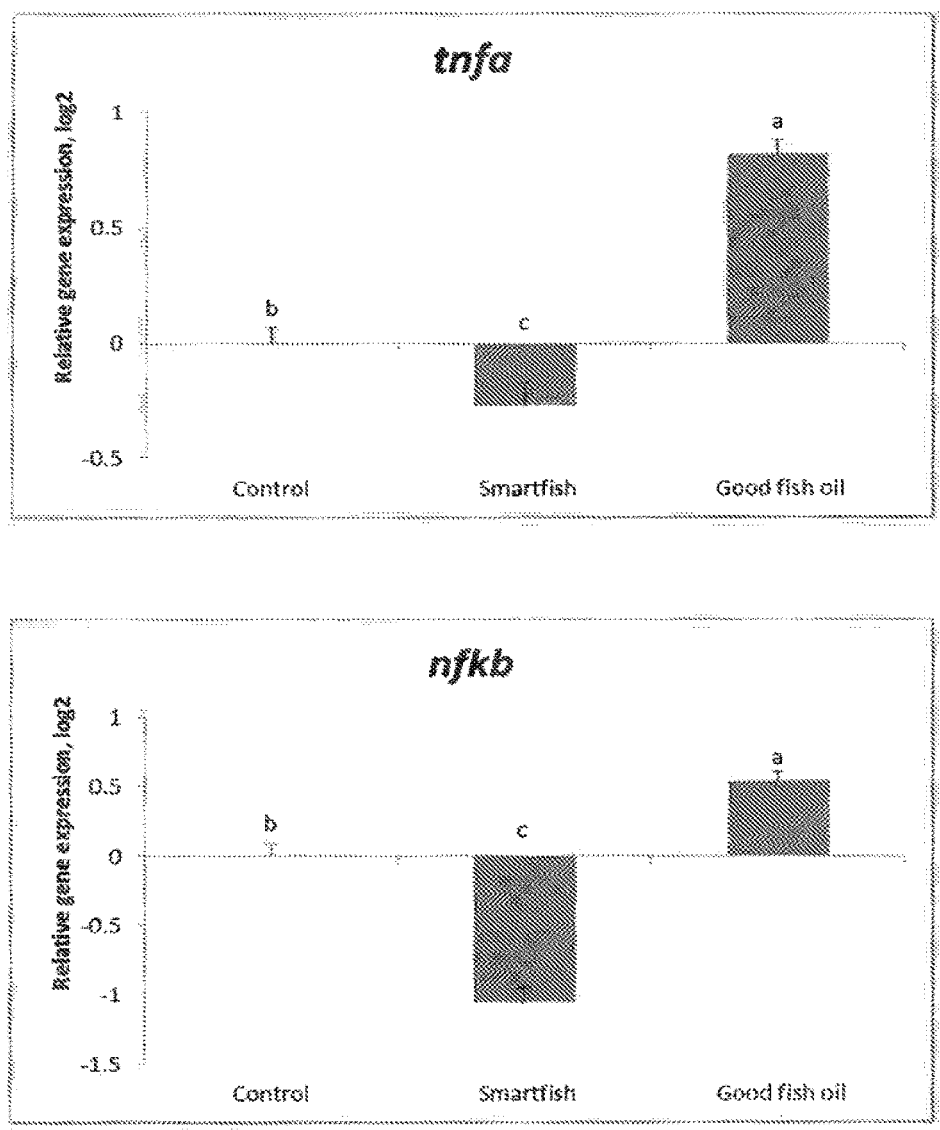
FIG. 7 illustrates the gene expression of tnfα and nfκb in LPS stimulated macrophages cultured in control media, media added a composition of the invention (Smartfish) or good fish oil.
Figure 8:
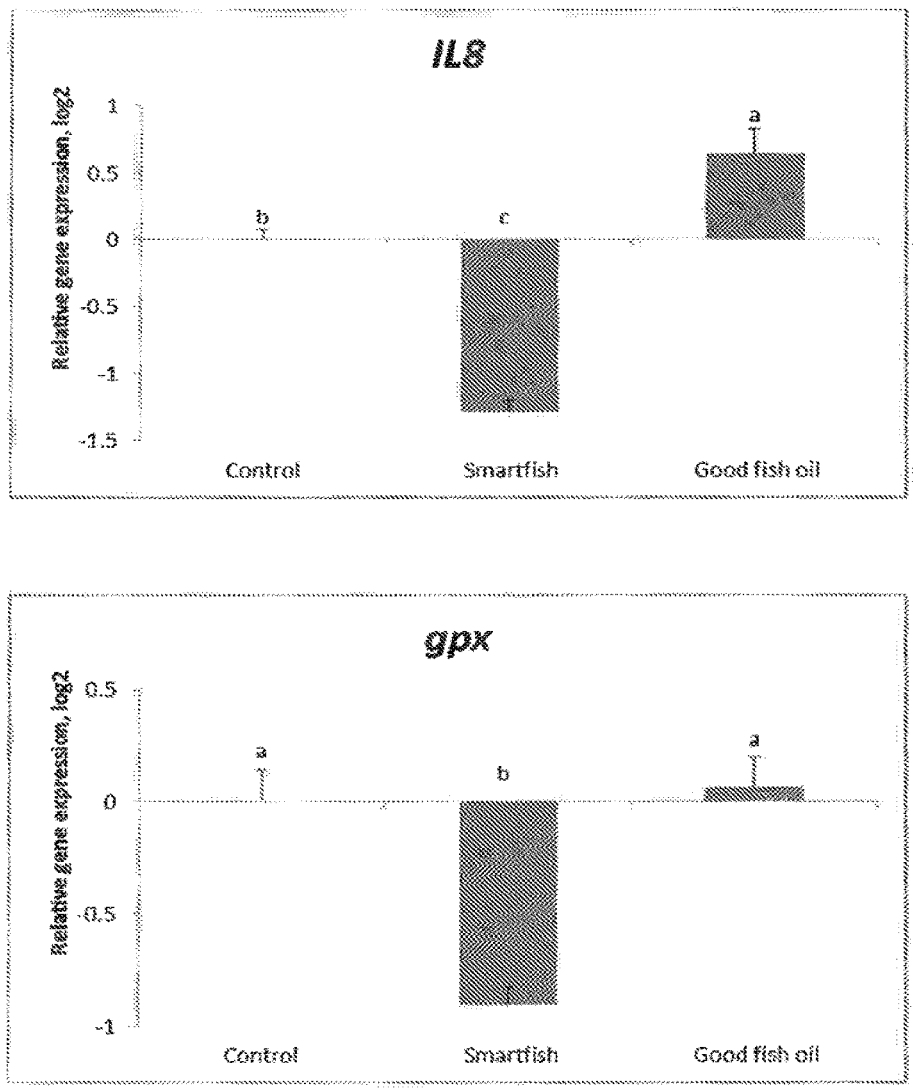
FIG. 8 illustrates the gene expression of IL8 in LPS stimulated macrophages cultured in control media, media added a composition of the invention (Smartfish) or good fish oil.
Figure 9:
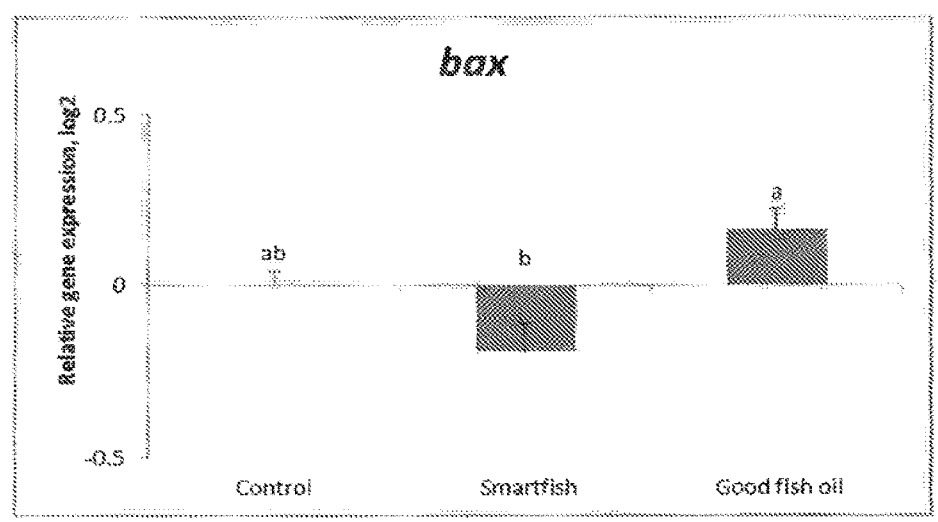
FIG. 9 illustrates the gene expression of bax and gpx in LPS stimulated macrophages cultured in control media, media added a composition of the invention (Smartfish) or good fish oil.

LPS induced macrophages cultured with Smartfish juice showed down-regulated gene expression of proinflammatory markers like tnfα, nfkb, and IL8, compared to control cells and cells cultured in media added good fish oil (FIGS. 7 and 8). Cells cultured in Smartfish juice also showed lower gene expression level of bax (involved in apoptosis) and tendency to lower gene expression of gpx (involved in oxidative stress response) than control cells and cells cultured in a good fish oil (FIG. 9).

From this study it has been demonstrated that Smartfish juice reduced the secretion of the proinflammatory cytokine TNF-α from human macrophages. Further it has been demonstrated that Smartfish juice reduced the expression of genes involved in inflammation and stress response (tnf-α, IL18, nfkb, gpx and bax) in human macrophages. The effect of Smartfish juice was significantly better than the just fish oil of similar good quality as the one used in the Smartfish juice.

Thus, it has surprisingly been shown that the composition of the invention comprising a combination of fish oil and juice in an oil-in-water emulsion, is useful use in treatment of inflammation and that a control good fish oil of similar quality as the fish oil contained in Smartfish juice did not reveal the same degree of positive effects of inflammatory parameters.

In particular, it was shown that the secretion of TNF-α was decreased and the gene expression of IL-8 was down-regulated. Modifications of said inflammatory markers are suggested to be of high relevance to COPD. See *Int J of Chronic Obstructive Pulmonary Disease* 2010:5 217-222; *Tumor necrosis factor-alpha levels in healthy smokers and nonsmokers* and Saris H. et al., *Biochem Pharmacol* 2010, Mar. 1; 79(5(:698-701; *IL-8 production by macrophages is synergistically enhanced when cigarette smoke is combined with TNF-alpha.*

Example 9

Resolvin Levels in Macrophages from AD Patients

The aim of the study was to examine the production of the anti-inflammatory mediator resolvin D1 and study whether the composition of the present invention (hereinafter identified Smartfish) has the ability to increase the amount of Resolvin D1 in cell samples from patients suffering from Alzheimers's disease.

As mentioned previously resolvins are oxygenated metabolites derived from EPA and DHA, having potent anti-inflammatory and immunoregulatory actions even in concentrations in the nanomolar and picomolar range.

Thus it is of great interest to see whether a composition of the invention have any impact on the level of resolvins in macrophages isolated from patients suffering from AD.

The composition of the invention used in this study is manufactured under the trademark Nutrifriend 2000, and is a fruit juice based drink containing 2000 mg EPA/DHA. The drink is manufactured by Smartfish AS and is hereinafter identified Smartfish.

Material and Methods

Patients supplemented with Smartfish will consume one fruit juice based drinks per day (i.e. 2000 mg EPA/DHA). Macrophages from AD patients were tested prior to and following at least 3 months of supplementation with Smartfish.

In Vitro Stimulation with Smartfish:

Macrophages from AD patients were prepared in cell culture from peripheral blood mononuclear cells (PBMCs) by culture in IMDM medium with 10% autologous serum for 10-15 days. When macrophages differentiated, they were treated overnight with or without Smartfish diluted 1:100 and were harvested into methanol, methanol was removed was removed by evaporation using nitrogen.

Resolvin D1 was tested by Resolvin D1 EIA kit #500380 (Cayman).

Resolvins are oxygenated metabolites derived from EPA and DHA, and a part of the molecular mechanisms contributing to removal of inflammatory cells and restoration of tissue once the need for inflammatory response is over.

Results

The level of RvD1 in macrophages of AD patients prior to supplementation with Smartfish was significantly increased when stimulated in vitro with Smartfish as outlined above. As set forth in Table 7 below, the RvD1 level increased from 8 to 13.6 pg in patient JB and from 37.4 to 75.9 pg in patient AM. Thus, a 2× increase in the level of RvD1 was observed following in vitro Smartfish stimulation of macrophages from AD patients not drinking Smartfish.

Similar analysis were done in patient JB following daily supplementation of one Smartfish per day. The RvD1 level increased from 8 to 21.3 pg in macrophages not stimulated in vitro. If further stimulated in vitro, the level of RvD1 increased moderately from 21.3 to 28.6 pg.

TABLE 7

| | RvD1 in macrophages (pg) | |
|---|---|---|
| | No in vitro stimulation with Smartfish | In vitro stimulation with Smartfish |
| Patient JB# 5 Dec. 2013 | 8 | 13.6 |
| Patient JB* 4 Mar. 2014 | 21.3 | 28.6 |
| Patient AM# 16 Jan. 20014 | 37.4 | 75.9 | before daily supplementation with the composition of the present invention
*after daily supplementation with the composition of the present invention for ~3 months The results from this study clearly showed that the composition of the invention contributed significantly to an increase in the resolvin level in macrophages from patients suffering from AD both in vivo and in vitro.

The study is ongoing, thus further results will be available in the future.

We claim:

1. A method for treatment of inflammation and/or disease/condition wherein an underlying cause is inflammation, the method consisting essentially of:
   administering to a human in need thereof a composition consisting essentially of a combination of fish oil, an emulsifier and juice in an oil-in-water emulsion,
   wherein said fish oil is selected from fish oil having a totox value below 20 and omega-3 content above 10% by weight based on the total weight of the fish oil,
   wherein said emulsifier is used to stabilize the emulsion,
   wherein said inflammation and/or disease/condition is selected from the group consisting of upper respiratory tract infection, amyotrophic lateral sclerosis, Alzheimer's disease, asthma, chronic obstructive pulmonary disease, cystic fibrosis, stroke, diabetes, traumatic brain injury, coronary disease, rheumatoid arthritis, and any combination thereof,
   wherein said juice is selected from the group consisting of pomegranate, apricot, grapefruit, orange, cranberry, rosehip, pineapple, black chokeberry, mulberry, cloudberry, acerola, raspberry, watermelon, peach, grapes, cherry, jambolao, apple, mango, pear, aronia, passion fruit, kiwi, and any combination thereof; and
   wherein said emulsifier is selected from the group consisting of milk solids, whey protein, oat protein, pea protein, and any combination thereof.

2. The method according to claim 1, wherein said inflammation and/or disease/condition is selected from the group consisting of upper respiratory tract infection, amyotrophic lateral sclerosis, Alzheimer's disease, asthma, chronic obstructive pulmonary disease, cystic fibrosis, diabetes, coronary disease, and any combination thereof.

3. The method according to claim 1, wherein the totox value of the fish oil is below 10.

4. The method according to claim 1, wherein the fish oil content is about 0.5 to 15% by weight based on the total weight of the composition.

5. The method according to claim 1, wherein the content of the juice is about 20-95% by weight based on the total weight of the composition.

6. The method according to claim 1, wherein the composition further consists essentially of pectin.

7. The method according to claim 1, wherein said composition is for administration at a dosage in the range from about 300 mg/day to about 5000 mg/day of EPA and DHA.

8. The method according to claim 7, wherein the composition is in a form selected from the group consisting of: liquid, capsule and powder.

9. The method according to claim 7, wherein said composition is for administration at a dosage of about 3000 mg/day of EPA and DHA.

10. The method according to claim 7, wherein said composition is for administration at a dosage of about 2000 mg/day of EPA and DHA.

11. The method according to claim 7, wherein said composition is for administration at a dosage of about 1100 mg/day of EPA and DHA.

* * * * *